(12) United States Patent
Kuzelka

(10) Patent No.: US 11,786,752 B2
(45) Date of Patent: Oct. 17, 2023

(54) METHODS AND SYSTEMS FOR SELF-STERILIZING TOUCH SCREEN

(71) Applicant: GE Precision Healthcare LLC, Milwaukee, WI (US)

(72) Inventor: Russell James Kuzelka, McFarland, WI (US)

(73) Assignee: GE Precision Healthcare LLC, Milwaukee, WI (US)

( * ) Notice: Subject to any disclaimer, the term of this patent is extended or adjusted under 35 U.S.C. 154(b) by 266 days.

(21) Appl. No.: 17/084,400

(22) Filed: Oct. 29, 2020

(65) Prior Publication Data

US 2022/0134128 A1    May 5, 2022

(51) Int. Cl.
*A61N 5/06* (2006.01)
*G06F 3/041* (2006.01)
*A61L 2/10* (2006.01)

(52) U.S. Cl.
CPC .............. *A61N 5/0624* (2013.01); *A61L 2/10* (2013.01); *G06F 3/0412* (2013.01); *A61L 2202/11* (2013.01); *A61N 2005/0652* (2013.01)

(58) Field of Classification Search
CPC ..... A61N 5/0624; A61L 2/10; A61L 2202/11; G06F 3/0412
See application file for complete search history.

(56) References Cited

U.S. PATENT DOCUMENTS

| | | | |
|---|---|---|---|
| 8,431,910 B1* | 4/2013 | Perry | ................ A61L 2/10 250/455.11 |
| 2016/0045633 A1* | 2/2016 | Pagan | ............... G02B 19/0019 250/455.11 |
| 2020/0215213 A1* | 7/2020 | Bryant | ................ G06F 1/1601 |
| 2021/0000991 A1* | 1/2021 | Kraus | ................ A61L 2/24 |

FOREIGN PATENT DOCUMENTS

| | | | |
|---|---|---|---|
| DE | 202020001197 U | * | 4/2020 |
| EP | 3043244 A1 | * | 7/2016 |
| WO | WO 2019/003197 A1 | * | 1/2019 |

OTHER PUBLICATIONS

English translation DE 202020001197 U (Year: 2020).*
English translation WO 2019/003197 A1 (Year: 2019).*

* cited by examiner

*Primary Examiner* — Sean E Conley

(57) ABSTRACT

Various methods and systems are provided for a self-sanitizing touchscreen in a liquid crystal display of a medical device. In one example, ultraviolet light of a first wavelength may be generated from one or more light emitting diode (LED) engines positioned along a perimeter of the touchscreen or integrated in the LCD assembly to sanitize the touchscreen, the ultraviolet (UV) light flooding the touchscreen to sanitize the touchscreen.

12 Claims, 14 Drawing Sheets

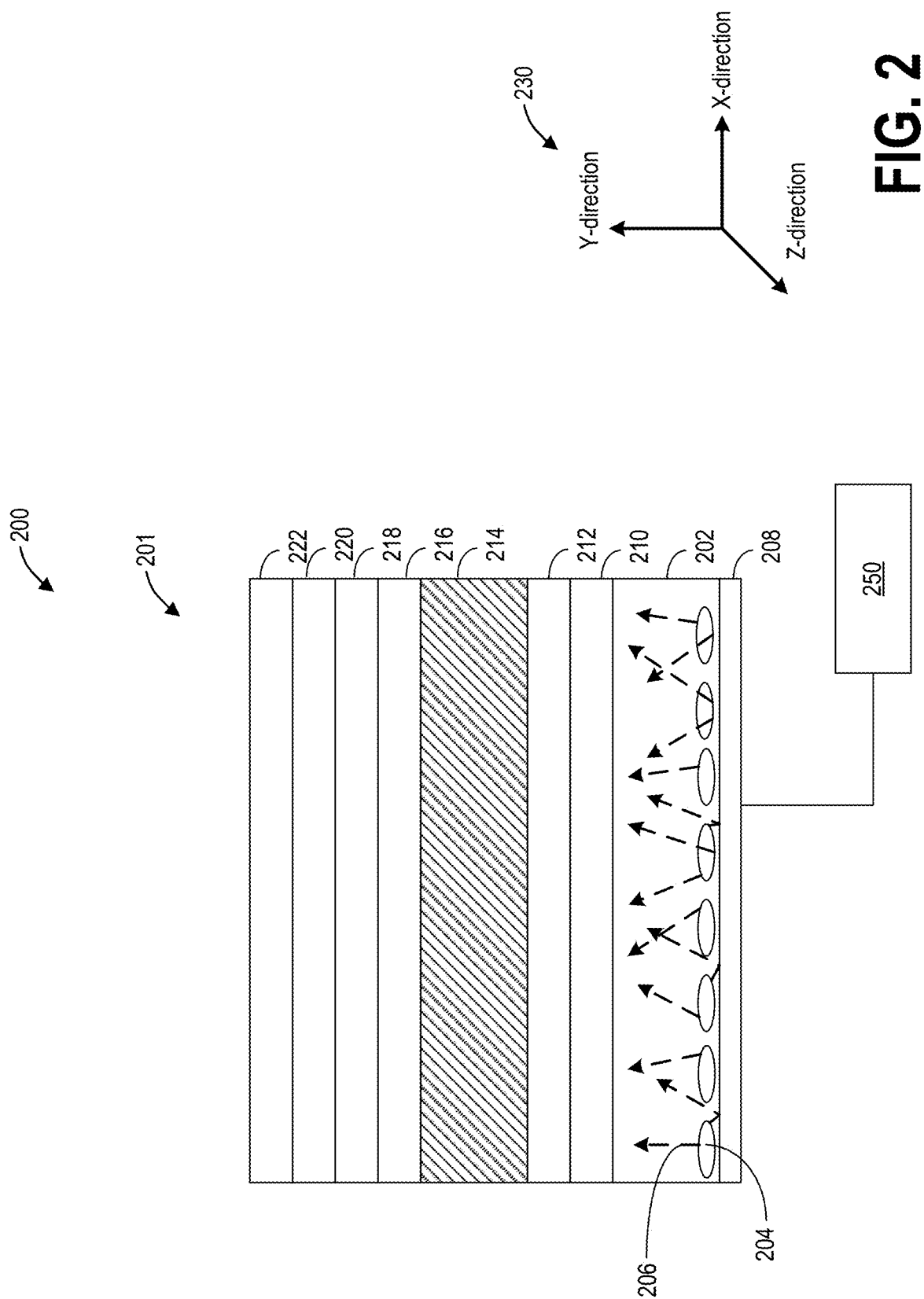

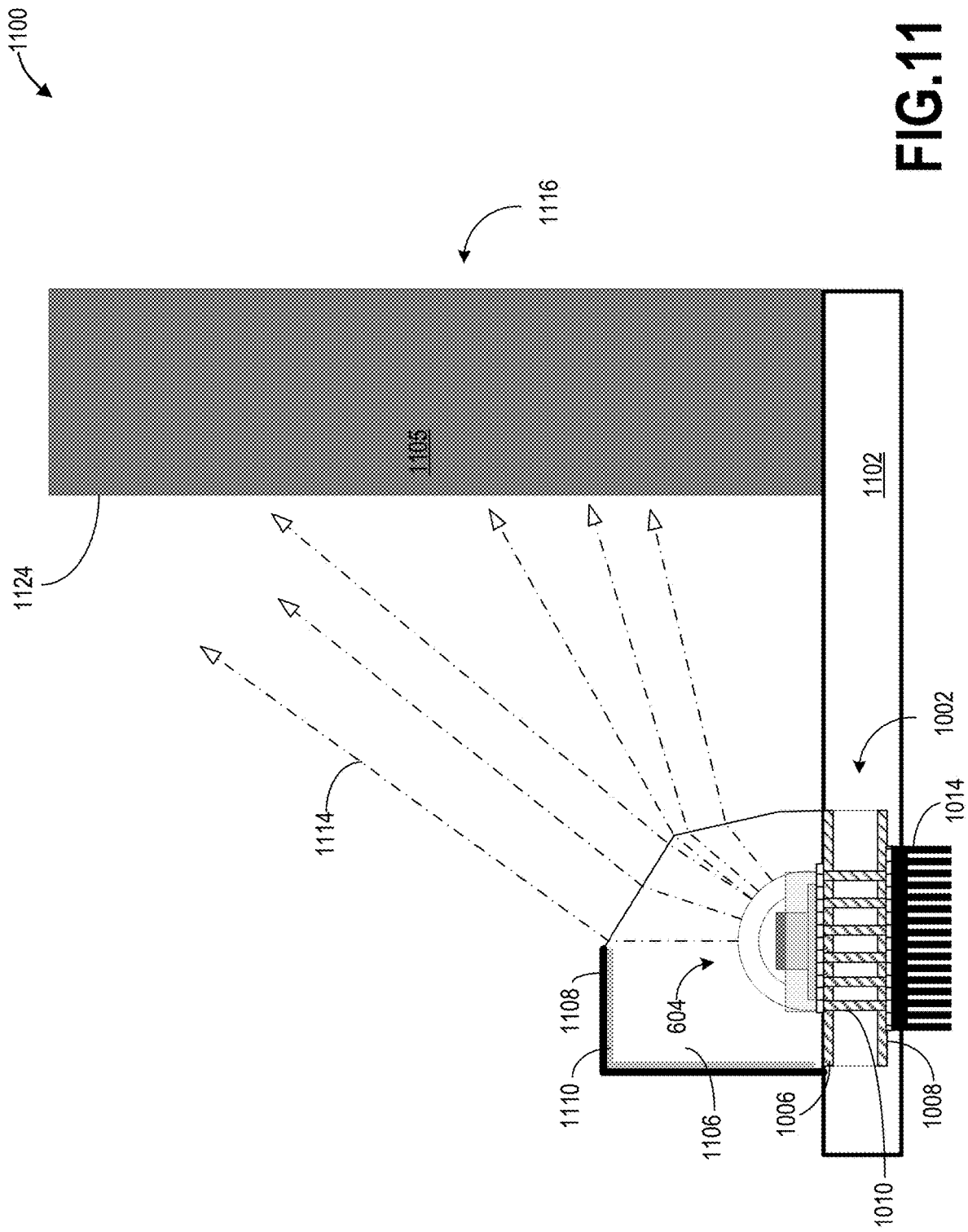

METHODS AND SYSTEMS FOR SELF-STERILIZING TOUCH SCREEN

FIELD

Embodiments of the subject matter disclosed herein relate to self-sterilization of a touchscreen surface, and more particularly, to a touchscreen surface in a medical device.

BACKGROUND

Medical devices may include a user interface with a display such as a liquid crystal display (LCD) which may be electronically activated such as using a touch pad and/or a touchscreen. The touchscreen display may be configured to present visual information such as in the form of text and graphics to an operator of the medical device. The touchscreen display may be used by the operator to enter commands and visualize patient data during operation of the medical device. Multiple operators may have access to a medical device and each operator may use the same touchscreen display during operation of the medical device. Medical devices configured with a touchscreen may include ventilator systems, anesthesia providing devices used in intensive care units and operation theaters, diagnostics equipment, etc.

As multiple operators access touchscreen display of a device, infectious pathogens may contaminate the display increasing a bacterial/viral load on the screen. Also, due to the touchscreen display being accessed by multiple medical professionals caring for different patients may increase a possibility of cross-contamination between patients. A cleaning routine for the touchscreen display is employed to reduce the possibility of transfer of pathogens via the display.

BRIEF DESCRIPTION

In one embodiment, a method, comprises: in response to a request for sterilization of a touchscreen included in a liquid crystal display (LCD) assembly of a medical device, generating ultraviolet light of a first wavelength from one or more light emitting diode (LED) engines positioned along a perimeter of the touchscreen or integrated in the LCD assembly, the ultraviolet (UV) light flooding the touchscreen to sterilize the touchscreen. In this way, ultra violet light may be effectively used for self-sterilization of a display.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

FIG. 2 shows a cross-sectional view of a first embodiment of a LCD display assembly including a self-sterilizing touch panel.

FIG. 11 shows a cross-sectional view of a LCD display assembly including a heat sink for cooling a LED engine.

DETAILED DESCRIPTION

Figure 1B:
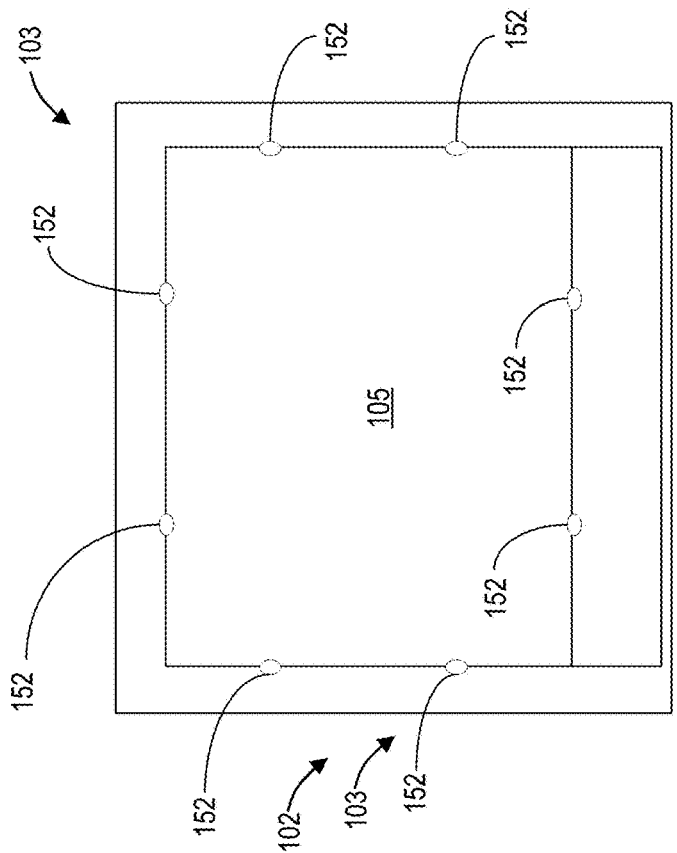
FIG. 1B shows the self-sterilizing touchscreen LCD display including LED engines emitting ultraviolet radiations.
Figure 1A:
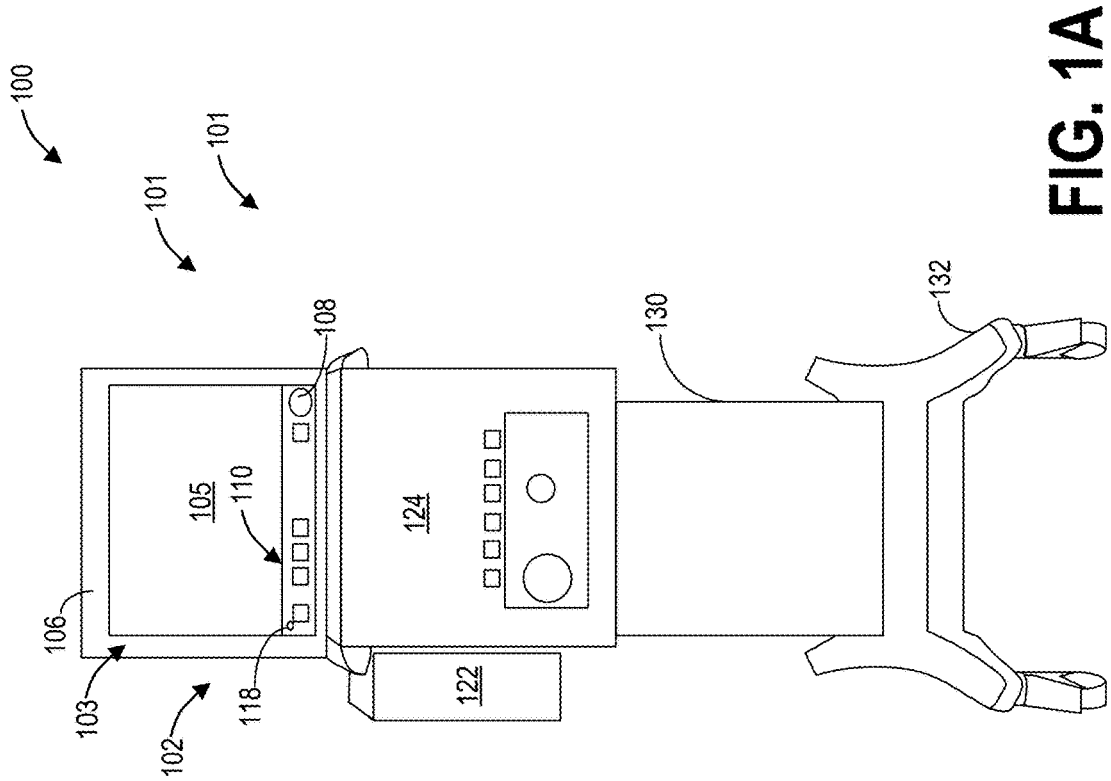
FIG. 1A shows a pictorial view of a ventilator system including a self-sterilizing touchscreen liquid crystal display (LCD).
Figure 4B:
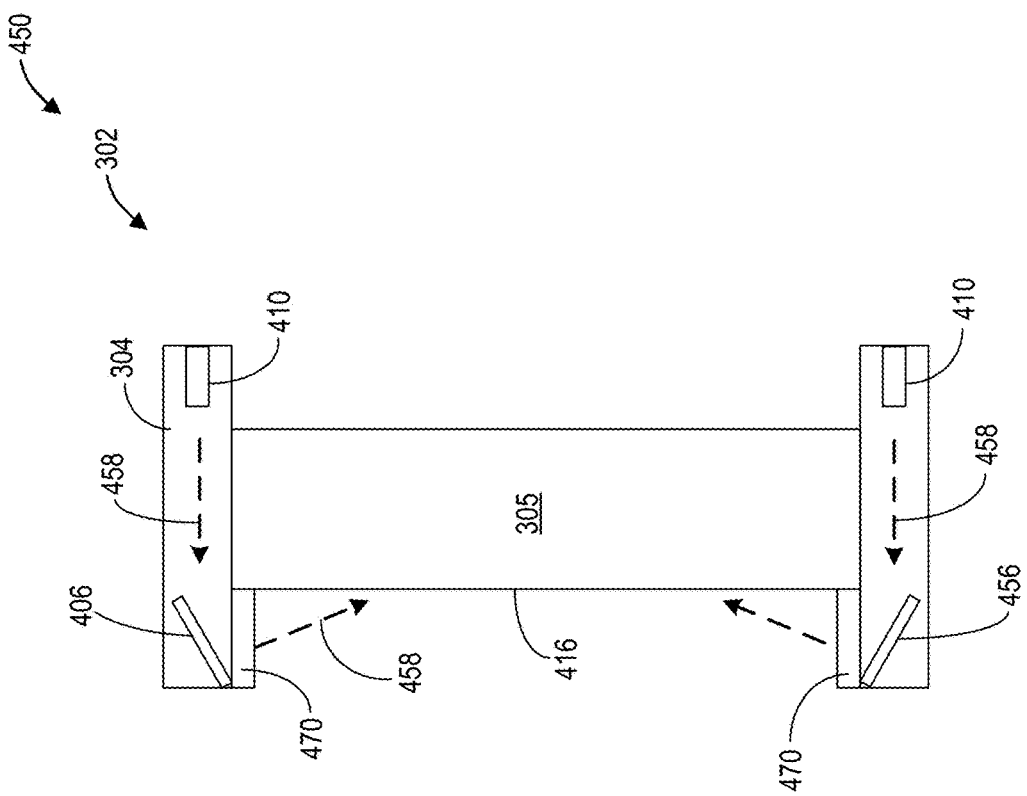
FIG. 4B shows a second cross-sectional view of the second embodiment of the self-sterilizing LCD display.
Figure 4A:
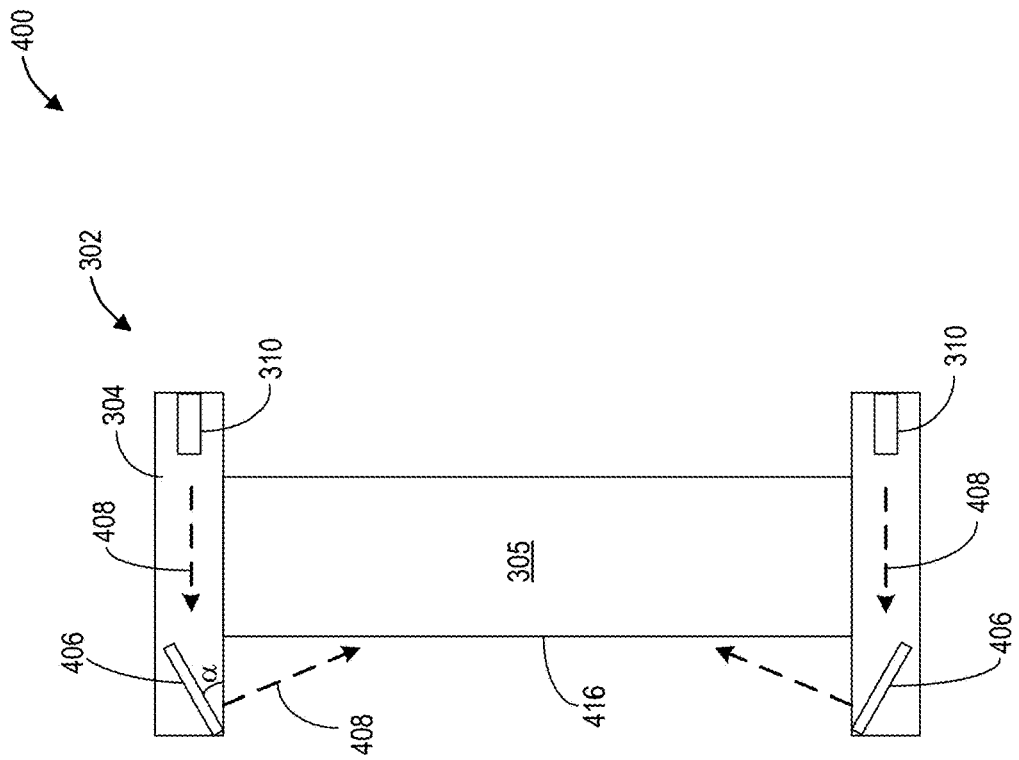
FIG. 4A shows a first cross-sectional view of the second embodiment of the self-sterilizing LCD display.
Figure 5B:
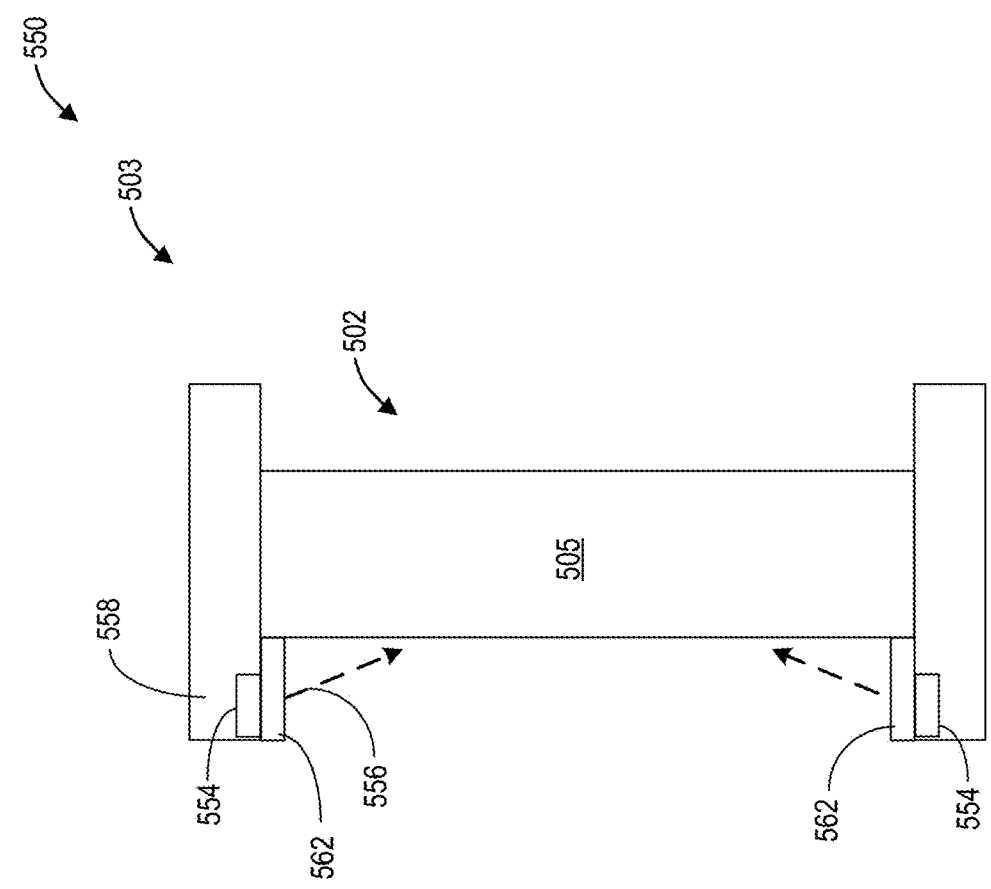
FIG. 5B shows a second cross-sectional view of the frame snapped on to a LCD display for sanitizing the LCD display.
Figure 5A:
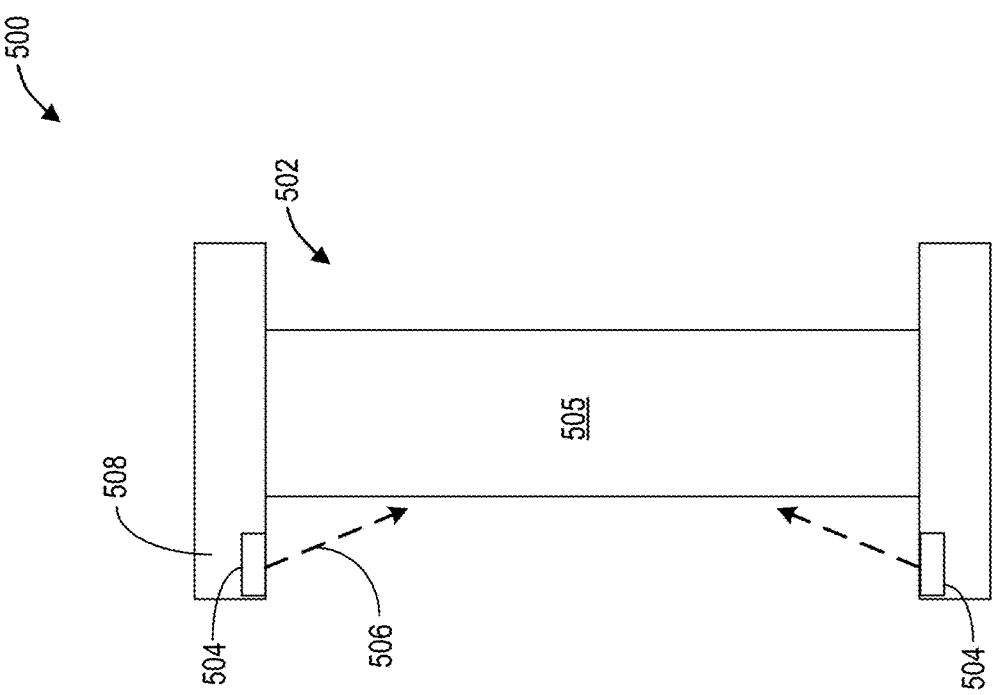
FIG. 5A shows a first cross-sectional view of a frame snapped on to a LCD display for sanitizing the LCD display.
Figure 6:
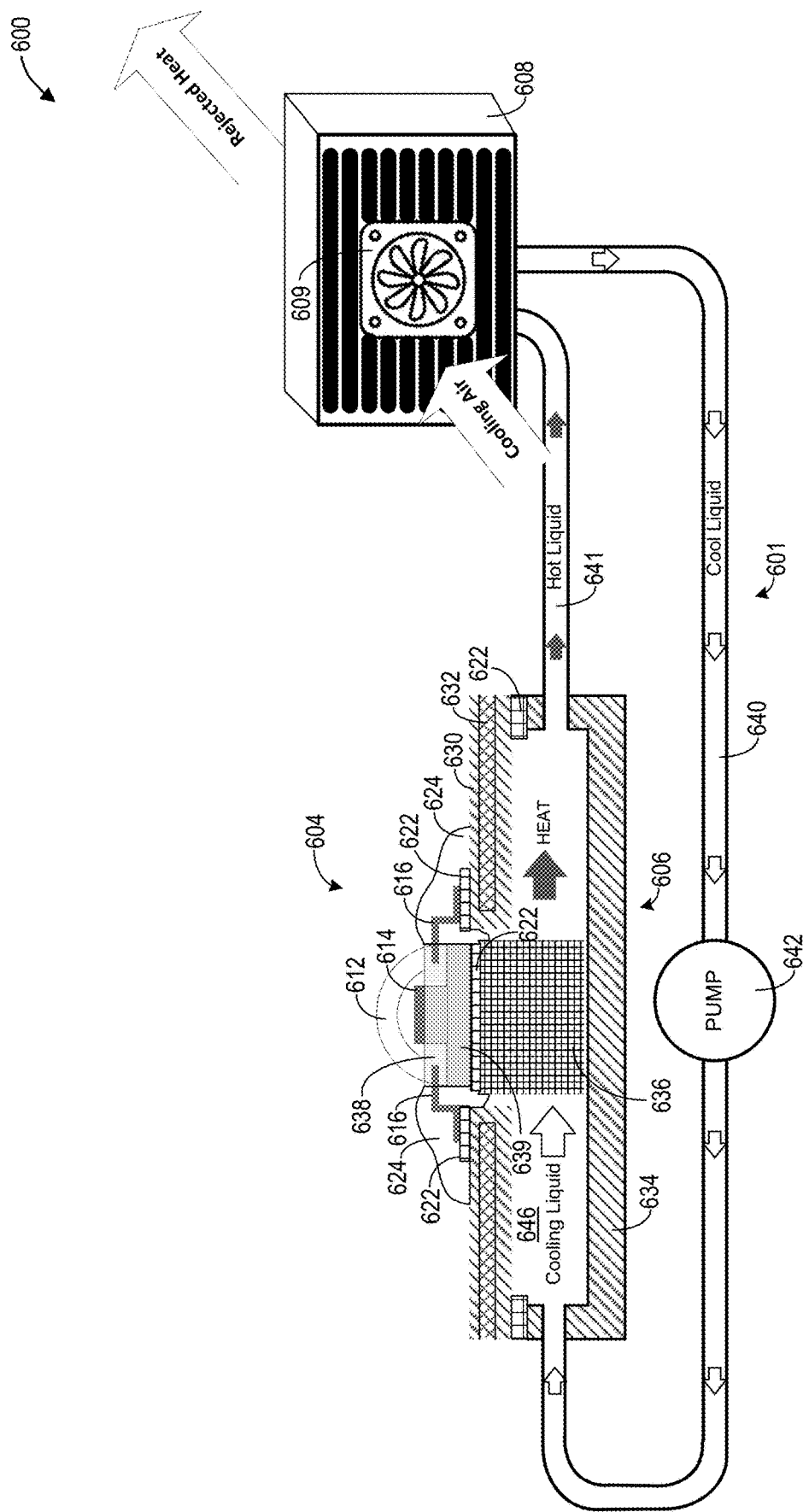
FIG. 6 shows a first example of a cooling system for a LED engine used for self-sterilizing a LCD display.
Figure 7:
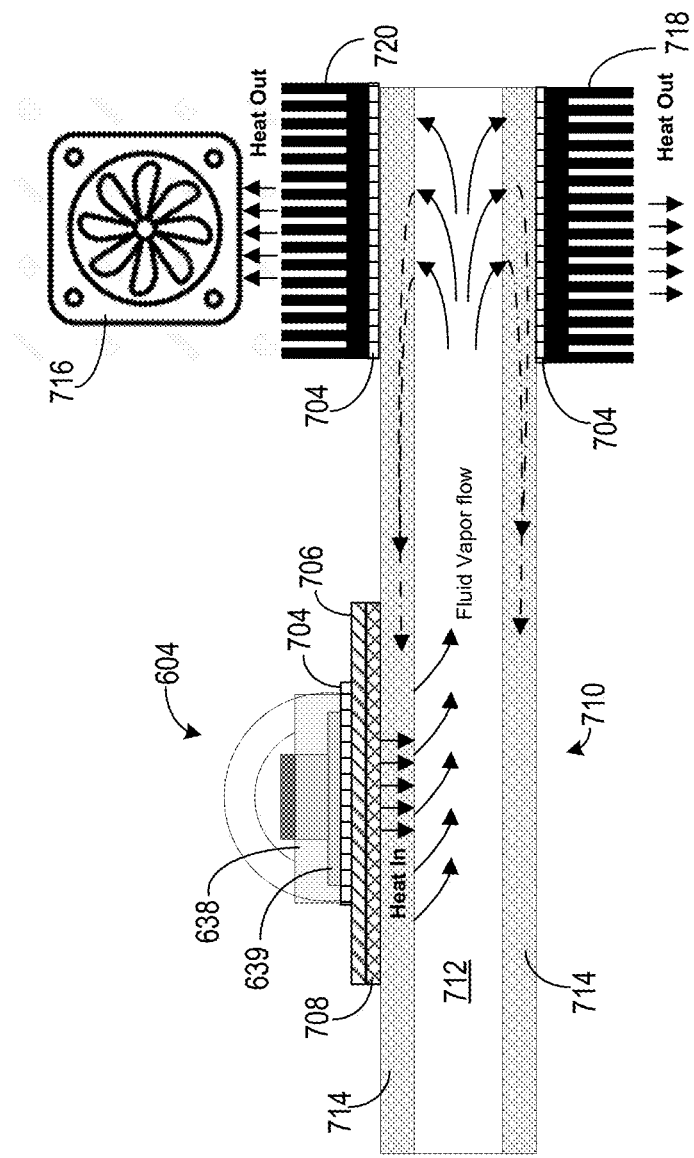
FIG. 7 shows a first example of a heat pipe for cooling a LED engine used for self-sterilizing a LCD display.
Figure 8:
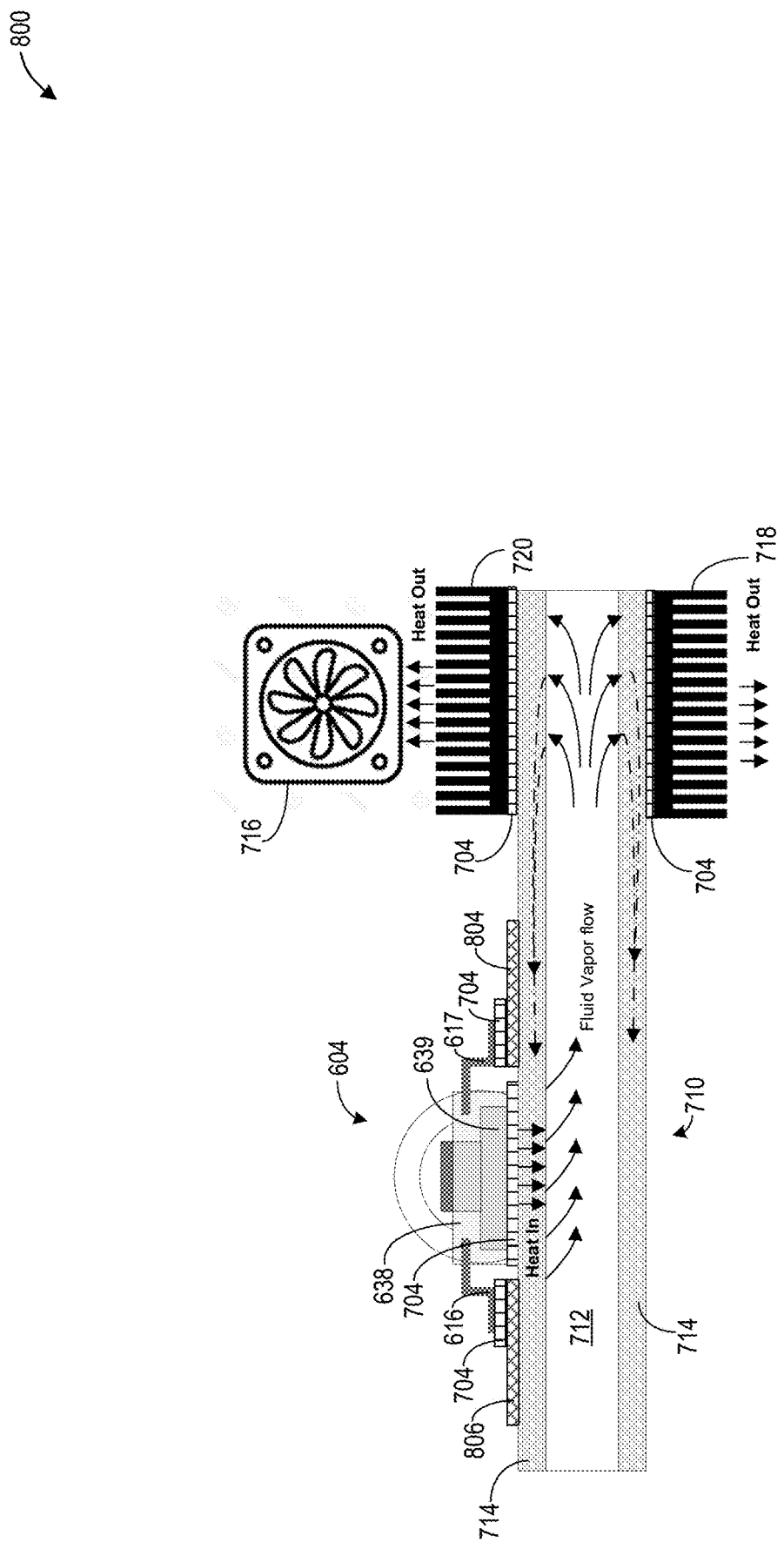
FIG. 8 shows a second example of a heat pipe for cooling a LED engine used for self-sterilizing a LCD display.
Figure 9:
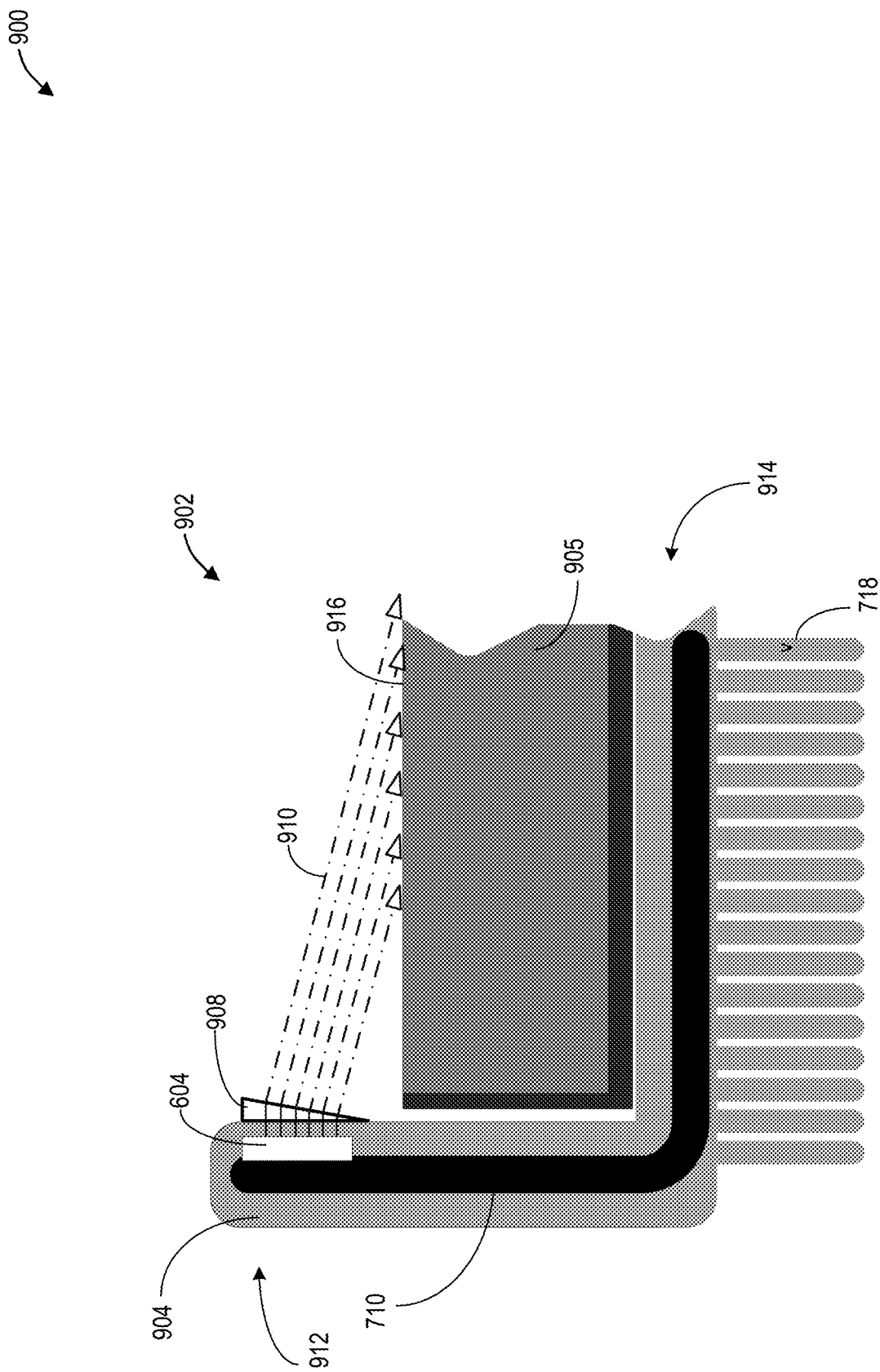
FIG. 9 shows a top down view of a LCD display assembly including a heat pipe for cooling a LED engine.
Figure 10A:
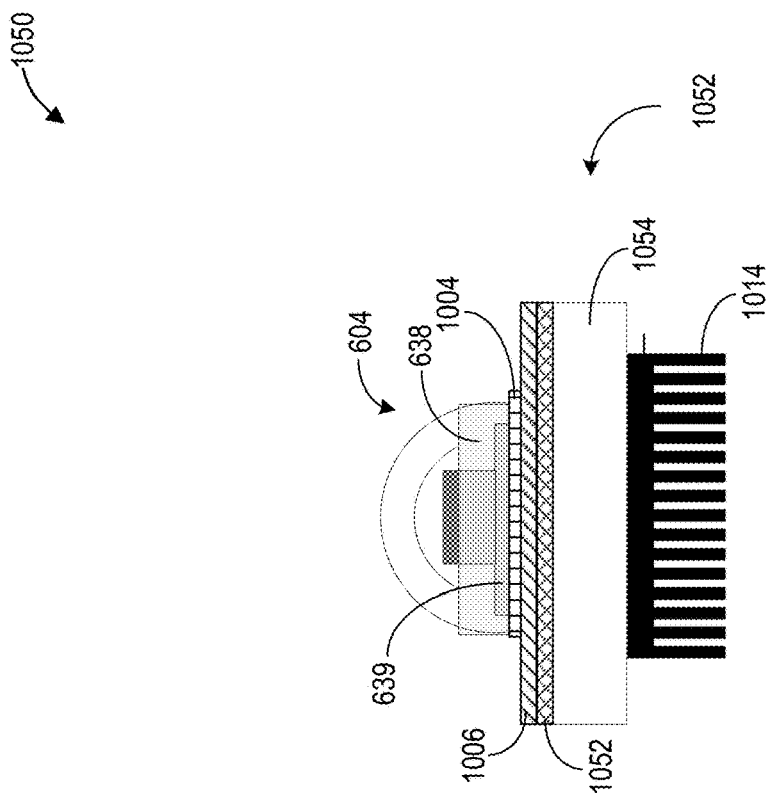
FIG. 10A shows a first example heat sink for cooling a LED engine used for self-sterilizing a LCD display.
Figure 10B:
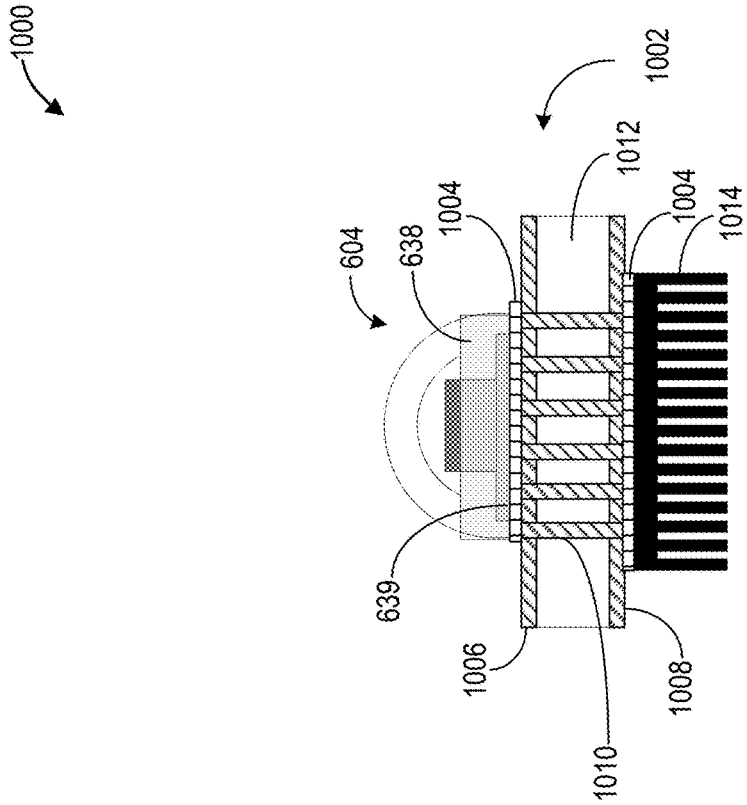
FIG. 10B shows a second example heat sink for cooling a LED engine used for self-sterilizing a LCD display.
Figure 12:
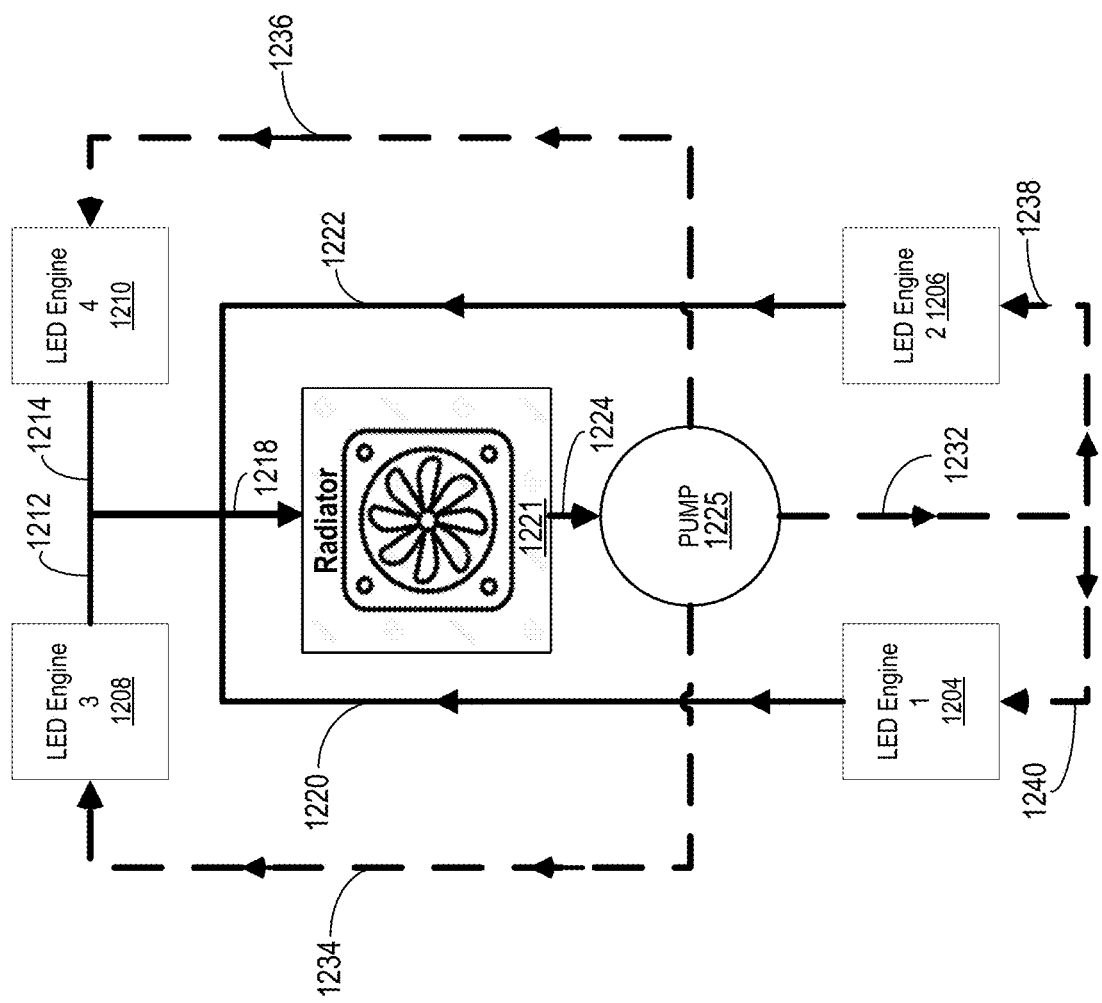
FIG. 12 shows a first example layout of passageways for fluidic cooling of one or more LED engines.
Figure 13:
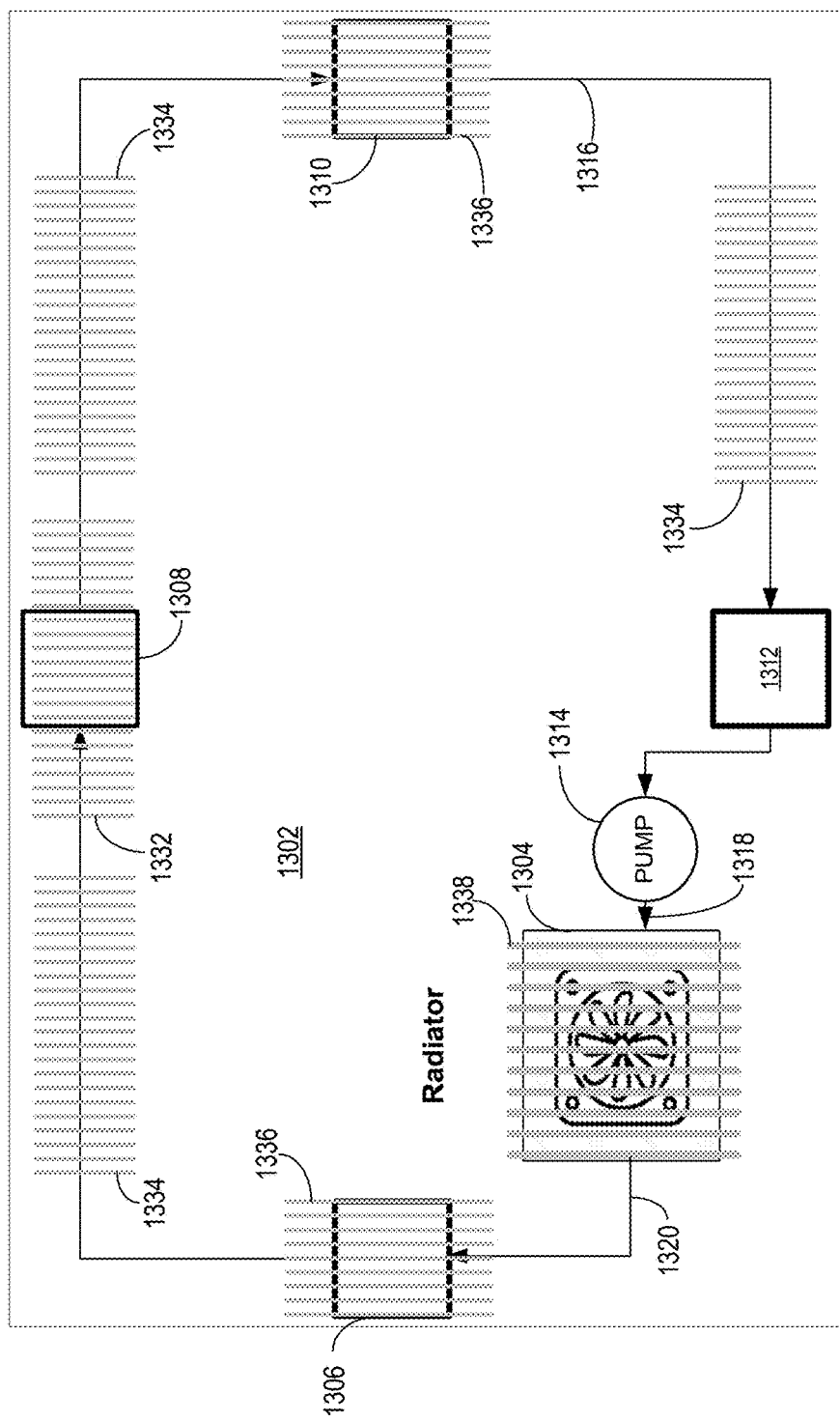
FIG. 13 shows a second example layout of passageways for fluidic cooling of one or more LED engines.
Figure 14:
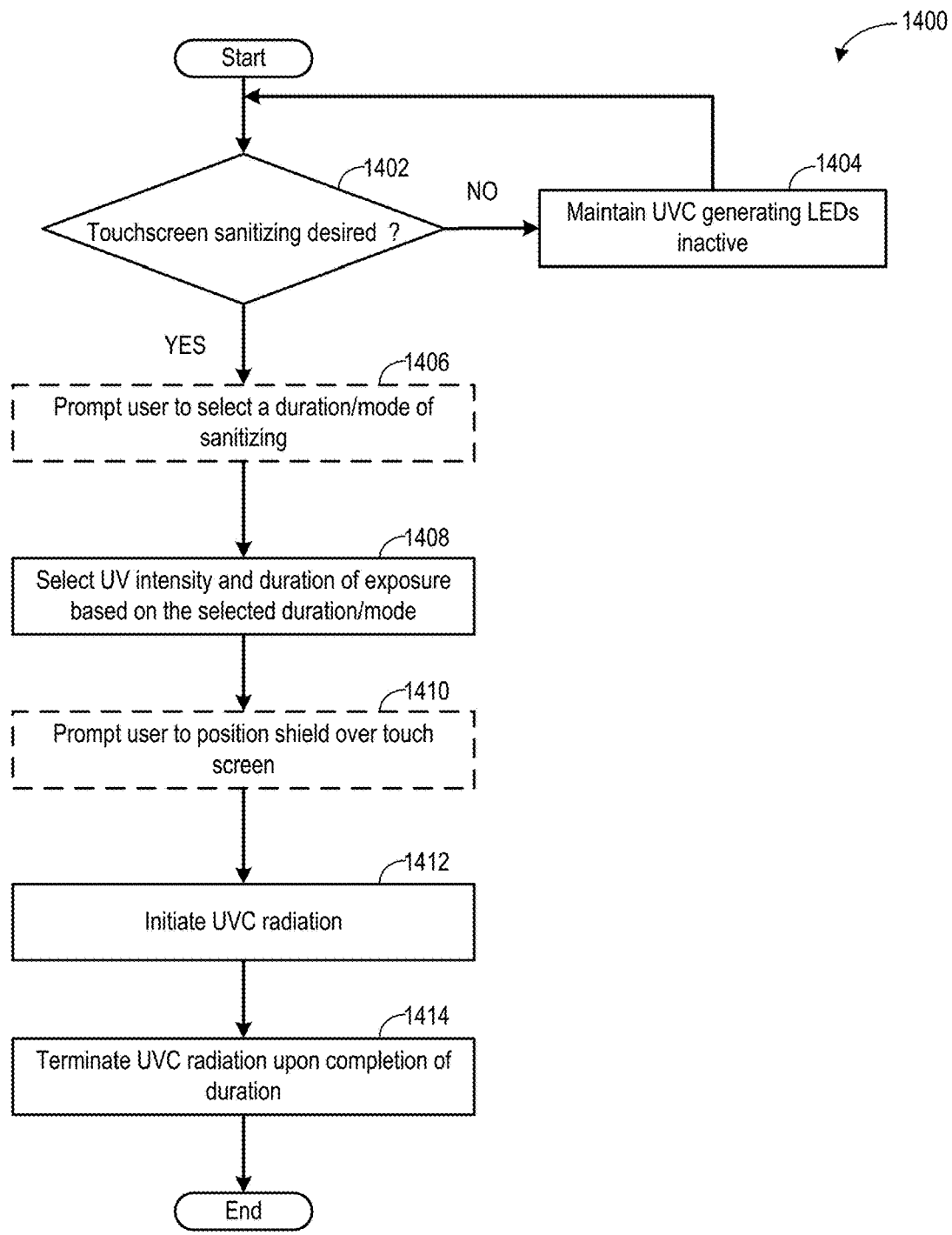
FIG. 14 shows a flow chart of an example method for sanitizing a touchscreen LCD display using UVC radiation.

The following description relates to various embodiments of a touchscreen LCD display equipped with self-sterilizing capabilities. In particular, systems and methods are provided for a self-sterilizing touchscreen of LCD display used in a ventilator system in a medical facility. An example embodiment of a ventilator system including a self-sterilizing LCD display including a touchscreen is shown in FIGS. 1A-B. A cross-section of a first embodiment of a self-sterilizing LCD display assembly including a backlight unit and a UVC emitting light emitting diode is shown in FIG. 2. A top view of a second embodiment of a self-sterilizing LCD display with UVC emitting LEDs embedded in a housing of the display. UVC radiation from the LED engines are configured to wash over the surface of the display. Cross-sectional views of the second embodiment of the self-sterilizing LCD display with UVC emitting LED engines embedded in the housing are shown in FIGS. 4A,4B. Cross-sectional views of a LCD display with a snapped on frame including UVC emitting LEDs are shown in FIGS. 5A, 5B. The frame including the LEDs are detachable from the LCD display. The LED engines may be cooled using a fluid based cooling system as shown in FIG. 6 or using a heat pipe as shown in FIGS. 7-9. Passageways for cooling fluid providing cooling to LED engines incorporated in a LCD display assembly is shown in FIGS. 12 and 13. LED engines may also be cooled via heat sinks as shown in FIGS. 10A, 10B, and 11. An example method for sterilizing a touchscreen LCD display using UVC radiation is shown in FIG. 14.

Though a ventilator system is described by way of example, it should be understood that the present techniques may also be useful when applied for self-sterilizing touchscreen displays used in other medical devices, such as an anesthesia providing device, x-ray imaging systems, magnetic resonance imaging (MM) systems, positron emission tomography (PET) imaging systems, single-photon emission computed tomography (SPECT) imaging systems, ultrasound imaging systems, and other diagnostics systems. The present discussion of a ventilator system is provided merely as an example of one suitable medical device.

Medical devices such as a ventilator system may include a user interface with a touchscreen display such as a liquid crystal display (LCD) overlaid with a touchscreen panel. The touchscreen panel may be used by a plurality of operators to enter commands, analyze results, and operate the medical device. Due to the touchscreen being frequently operated by multiple operators tending to different patients, pathogens such as virus and bacteria may contaminate the surface of the screen. Such pathogens on the display can increase a possibility of cross-contamination between patients. With an increase in patient loads in medical facilities and a lack of staff members, cleaning of touchscreen surfaces between two users may be inadequate in reducing the pathogen load on the surface.

In one example, radiations at certain ultraviolet (UV) wavelengths may be effective in killing microorganisms such as bacteria and virus effectively regardless of their drug-resistant proficiency. Further, UVC radiation in the wavelength range 200-222 nm may effectively sterilize a surface without being detrimental to human skin and eye sight. As an example, the single wavelength far-UVC light of 207 nm has been studied to effectively kill bacteria without apparent harm to human skin tissue, The 207 nm UV light has a short range in biological material, as it cannot penetrate the human stratum corneum (the dead-cell skin layer, with a thickness of 5-20 um) nor the cytoplasm of individual cells. However, the 207 nm UV light can penetrate bacteria and viruses as their cells are physically much smaller. An array of LED engines emitting UVC radiation in the desired wavelength range may be integrated and/or positioned along a perimeter of a LCD display to saturate the surface of the touch screen with UVC radiation in order to kill pathogens and disinfect the surface between uses of the touch screen by two separate users.

In a first embodiment, an array of LED engines may be embedded within a backlight of the LCD assembly. In a second embodiment, an array of LED engines may be positioned along the perimeter (such as along a frame or bezel around the display) of the display panel. In a third embodiment, a standalone, detachable frame including an array of LED engines positioned along the surface of the frame may be snapped onto a display. The LED engines may be angled to propagate the UVC radiation towards the display. Quartz optics may be used to reflect and direct the UVC radiation from the perimeter of the display (integrated or snapped on frame) to the surface of the display such that the touchscreen is saturated with the UVC radiation. In one example, LEDs emitting UVC radiation in a wavelength of 200-222 nm may be used. In another example, commonly available broadband LEDs emitting UVC radiation in a wavelength of 254 nm may be used along with an optical bandpass filter such that radiation in the range of 200-222 nm (such as a wavelength of 207 nm) reach the screen.

An operator may initiate a sanitizing routine of the display by making a selection via the touchscreen of the display and/or via a remote device such as a smart phone. The operator may also select a mode of operation of the self-sanitizing routine and/or a duration of sanitization that is desired to be carried out. Based on the selected mode and/or a desired duration, the intensity of the UVC and the duration of exposure may be adjusted to regulate a dosage of UVC delivered within the desired time window for sterilization of the display.

In this way, by incorporating sources of UVC light within a touchscreen display, sterilization of the display may be carried out without use of any external agents/chemicals or man power. The technical effect of using a UV light in the wavelength of 200-222 nm (such as 207 nm) is that the microorganism may be effectively killed without the radiation being able to penetrate through dead cell layer of human skin or tear layer of the eye. The UVC radiation may be effectively used to kill novel viruses and antibiotic resistant bacterial loads. By disinfecting frequently touched displays as part of a patient/room turn over workflow, a sterilized touchscreen may be available to each new user, thereby reducing the possibility of cross-contamination. Overall, by using self-sterilizing touchscreen displays, hygiene of operating a medical device may be improved and spread of pathogens within a medical facility may be reduced.

FIG. 1A shows an example embodiment 100 of a ventilator system 101 including a touchscreen liquid crystal display (LCD) assembly as user interface (UI) 102. FIG. 1B shows a self-sterilizing touchscreen 105 of the LCD assembly 103 including a series of LED engines. The ventilator system 101 is designed to ventilate a patient's lungs with breathing gas such as oxygen, and to thereby assist a patient with breathing when the patient's ability to breathe on their own is impaired.

The ventilator system 101 may include a ventilator that supplies a breathing gas to the lungs of a patient via a breathing circuit that may comprise an inspiratory line, an expiratory line, and a patient connection tube. The ventilator may be included within a housing 124 of the ventilator system 101. Breathing gas from the ventilator may be supplied to the patient via a $CO_2$ absorber, a humidifier, and the inspiratory line. Air expired by the patient is recycled to the ventilator via the expiratory line. As an example, a positive pressure ventilator may include a compressible air reservoir or turbine. The air reservoir may be pneumatically compressed several times a minute to deliver an air/oxygen mixture (breathing gas) to the patient. A turbopump may also be used to push air through the ventilator with a flow valve adjusting a pressure of breathing gas to meet patient-specific parameters.

The ventilator system 101 may include a UI 102 comprising a LCD assembly 103. The LCD assembly 103 may include a touchscreen 105. The LCD display 103 may include a frame 106 lining perimeter of the touchscreen 105. The touchscreen 105 may be configured to present visual information such as in the form of texts, plots, and graphics to an operator of the ventilator system 101. The touchscreen 105 may be used by the operator to enter commands such as select a mode of operation of the ventilator. In one example, each mode may correspond to a pressure of breathing gas being delivered. The touchscreen 105 may also show data relating to patient's health conditions such as blood oxygen level, heart rate, temperature, etc.

The touchscreen 105 may be accessed by different operators as the ventilator system 101 may be used for different patients. Infectious pathogens may contaminate the touchscreen 105 increasing a bacterial/viral load on it. The touchscreen 105 may be sterilized by washing over substantially (such as more than 90%) the entire surface area of the touchscreen that comes in contact with an operator in common usage for example, with an ultraviolet radiation that is capable of destructing microorganisms including novel virus and bacteria, thereby sanitizing the touchscreen 105. As an example, the UV radiation may wash over more than 90% of the surface area of the touchscreen. As shown in FIG. 1B, a series of LED engines 152 lining the touchscreen 105 may be used to generate the UV radiation used to disinfect the touchscreen 105. In one example, as elaborated in FIGS. 4A, B, each of the LED engines 152 may be integrated in the frame 106 around the perimeter of the touchscreen 105. In one example, the frame 106 may be an integral part of the LCD assembly 103. In another example, as elaborated in FIGS. 5A, B, the frame 106 may be an independent, detachable structure that may be snapped onto the LCD assembly 103 during the sterilization of the touchscreen. The UV light generated from the LED engines 152 positioned along the perimeter of the LCD assembly 103 may be focused onto the touchscreen via one or more optical directors. In another embodiment, as discussed in FIG. 2, one or more LED engines may be integrated in a backlight unit of the LCD assembly 103, the UV light travelling through an array of liquid crystals, polarizers, and quartz substrates to reach a touchscreen panel of the LCD assembly 103.

Sterilization of the touchscreen 105 may be initiated in response to a sterilization cycle being selected by an operator via an input to the touchscreen 105 or via an input to a device wirelessly connected to the LCD assembly 103. The initiation of sterilization may also be in response to an end of a workflow and completion of use of the ventilator system 101 by an operator or a patient. An intensity of the UV light may be adjusted based on a duration of sterilization of the touchscreen 105 and a desired dosage of the UV light, the intensity of the UV light increasing with an increase in the desired dosage and a decrease in the duration of sterilization. UV light in a wavelength range of 200 nm and 222 nm may be used for the sterilization process.

When microorganisms are exposed to deep (far) UV light in the range of 200 nm to 300 nm it is absorbed by DNA, RNA, and proteins of the microorganisms. Absorption by proteins may lead to rupture of cell walls and death of the organism. Absorption by DNA or RNA (specifically by thymine bases) is known to cause inactivation of the DNA or RNA double helix strands through the formation of thymine dimers. Upon creation of dimers in DNA, the DNA replication process is disrupted, and the cell cannot replicate. UVC light in the wavelength range 200-222 nm not only possess the ability to kill microorganisms but also can be used without detrimental effects to human skin and eyes. The narrow wavelength range of 200-222 nm may be significantly harmful to microorganisms such as bacteria but may not cause any damage to cells in tissues.

The UI 102 may include a set of hard keys 110 or buttons to be used during operation of the ventilator system 100. The hard keys 110 or buttons may enable the operator to change audio settings, increase flow of breathable gas, lock/unlock system, and return to a home settings to access associated features. A knob 108 may be included in the UI 102 which may be turned clockwise and anticlockwise to change a setting, the knob 108 may also be pressed to confirm a setting. An LED indicator 118 may be lit up when the ventilator is connected to a main power supply and an internal battery of the ventilator system 101 is being charged. The housing 124 may also include a series of hard keys.

A computing device 122 may be included in the ventilator system 101 to operate the ventilator based on operator-supplied and/or system-defined commands and parameters. The computing device 122 may be configured as a conventional computer including a microprocessor unit, input/output ports, read-only memory, random access memory, keep alive memory, a controller area network (CAN) bus, etc. The ventilator system 101 may include a pedestal 130 mounted on a trolley 132 with wheels which may increase mobility of the assembly.

FIG. 2 shows a cross-sectional view 200 of a first embodiment of a LCD assembly 201 including a self-sterilizing touch panel. The LCD assembly 201 may be the LCD assembly 103 of FIGS. 1A,B. In the first embodiment, the UVC emitting LEDs are integrated in the LCD assembly. The LCD assembly 201 may include a plurality of components (shown here as layers) stacked vertically along a y-direction of the coordinate system 230.

A first, lower most, component is a backlight unit 202 including an array of UVC light emitting diode (LED) engines 204. An LED engine may be an integrated assembly composed of one or more light emitting diodes (LEDs) or LED arrays (modules), as well as an LED driver and other optical, thermal, mechanical and electrical components. The LED engines are ready-to-light and may only require an input voltage. Details of an LED engine is elaborated in FIG. 6.

The LED engines 204 may be embedded in one or more layers within the backlight unit 202. The LED engines may be configured to radiate UVC light in the wavelength range of 200-222 nm through the components of the assembly, in a positive y-direction, as shown by the arrows 206. The lower surface and side walls of the backlight unit may be coated with a reflective material 208 such as microporous PTFE Porous PTFE (polytetrafluoroethylene) or polished aluminum such that any UVC ray travelling in the negative y-direction may be reflected back (from the reflective material 208) towards the top of the assembly. The UVC emitted in the backlight unit 202 may travel to the topmost layer (touch panel 222) through the vertically stacked components of the display assembly. The LED engines 204 may be powered by an electric circuit (not shown) of the display. The backlight unit 202 may also include one or more sources of visible light (not shown) providing a backlight for the display.

In one example, an easily available and cost effective broadband LED light of wavelength 254 nm may be used in the backlight unit along with a layer of optical bandpass filter positioned within the backlight unit 202 above the LED engines to selectively pass through UVC in the wavelength range 200-222 nm to the top layer of the display assembly.

The second component above the backlight unit 202 is a first polarizer 210. The first polarizer may be a horizontal polarizer. The first polarizer 210 may be used to polarize light made incident to the liquid crystal array positioned vertically above it to adjust transmittance of light, thus facilitating a desired image formation. The first polarizer 210 may block all light waves except those vibrating horizontally.

The third component above the first polarizer 210 includes a first substrate 212 including data lines, gate lines, thin film transistors (TFTs) and various electrodes such as pixel electrode, or the like, formed therein. The first substrate 212 may also be referred as TFT array substrate. The first substrate may be made of quartz instead of regular glass. Quartz is transparent to the UVC radiation being transmitted from the backlight unit 202 to the topmost layer (touch panel 222) via each of the intermediate layers including the first substrate 212.

The fourth component above the first substrate 212 is an array of liquid crystals 214. The liquid crystals may be sandwiched between a negative electrode and a positive electrode with a voltage difference applied across the liquid crystal layer. The liquid crystal, also termed as twisted nematics (TN), may be naturally twisted. Applying an electric current to these liquid crystals may untwist them to varying degrees, depending on the current's voltage. Such liquid crystals are used in the array 214 because they react predictably to electric current in such a way as to control light passage through the LCD.

The fifth component above the array of liquid crystals 214 includes a second substrate 216. The second substrate 216 may include black matrices and color filter layers 218 formed on a surface of the second substrate. The second substrate 216 may be made of quartz instead of regular glass. Quartz being transparent to the UVC radiation, the UVC may be transmitted from the backlight unit 202 to the topmost layer (touch panel 222) via each of the intermediate layers including the second substrate 216.

The sixth component above the second substrate 216 is a second polarizer 220. The second polarizer 220 may be a vertical polarizer. The second polarizer 220 may be used to polarize light emitting from the liquid crystal array positioned below it to adjust transmittance of light, thus facilitating a desired image formation. The second polarizer 220 may block all light waves except those vibrating vertically. The axes of transmission of the first polarizer and the second polarizer may be perpendicular to each other.

An array of liquid crystal may form a pixel and a display includes a plurality of pixels. During a first condition, when a pixels in the LCD display is switched off, visible light may travel from the backlight unit 202 toward the liquid crystal array 214. The first horizontal polarizer 210 in the path of the light blocks out all light waves except those vibrating horizontally. A transistor in the first substrate 212 may switch off this pixel by initiating flow of electricity flowing through its array of liquid crystals 214. The electricity flowing through the liquid crystals may cause the crystals to straighten out (such that they are completely untwisted), and the light travels straight through these crystals unchanged in polarity. Light waves emerge from the liquid crystals still vibrating horizontally. The second polarizer 220 above the liquid crystal array may block out all light waves except those vibrating vertically. The horizontally vibrating light that travelled through the liquid crystals may not pass through the vertical polarizer. Therefore, light may not reach a display at a point corresponding to the pixel and the pixel is dark.

During a second condition, when the pixels in the LCD display is switched on, visible light may travel from the backlight unit 202 toward the liquid crystal array 214. The first horizontal polarizer 210 in the path of the light blocks out all light waves except those vibrating horizontally. A transistor in the first substrate 212 may switch on this pixel by terminating flow of electricity through its array of liquid crystals 214. Due to the lack of electricity flowing through the liquid crystals, the crystals may twist. The twisted crystals rotate light waves by 90° as they travel through. Light waves that enter the array of liquid crystals 214 vibrating horizontally emerge from the array of liquid crystals 214 vibrating vertically. The second polarizer 220 above the liquid crystal array may block out all light waves except those vibrating vertically. Therefore, the vertically vibrating light that emerged from the liquid crystals may pass through the second polarizer 220. Therefore, light may reach a display at a point corresponding to the pixel and the pixel may be lit up. Color filter layers 218 including a red, blue, or green filter gives the pixel its color.

The seventh component above the second polarizer 220 is a touch panel 222 forming a touchscreen of the display. The touch panel may be a Projected Capacitive Touch panel that uses a conductive grid to recognize changes in its electromagnetic field by the touch of a finger. In alternate examples the touch panel 222 may be an infrared touch panel.

Upon activation of the LED engines 204 embedded in the backlight unit 202, UVC light may propagate through each of the above mentioned layers and reach the touch panel 222. As the UVC light floods the touch panel 222, it kills pathogens contaminating the panel and disinfects the touchscreen. In one example, a cover or flap (not shown) may be used to cover the touch panel 222 during generation of the UVC from the LED engines 204. In another example, it is also envisioned that the cover or flap may include an enable/lockout mechanism which would communicate (i.e., electronically, mechanically, optically) with the display to enable/disable the activation of the UVC LED engines. By positioning the flap on the touch panel 222, it may be indicated that a sanitizing routine is being carried out and the display may not yet be sterilized and ready to be used by an operator A controller 250 may be coupled to the LCD assembly 201 to operate the LCD assembly. The controller 250 may be configured as a conventional microcomputer including a microprocessor unit, input/output ports, read-only memory, random access memory, keep alive memory, a controller area network (CAN) bus, etc. Power to operate the LCD assembly may be provided through the controller 250.

An operator may initiate a sanitizing routine of the display by making a selection via the touch panel 222 of the display and/or via a remote device such as a smart phone. The operator may also select a mode of operation of the self-cleaning routine and/or a duration of sanitizing that is desired to be carried out. Based on the selected mode and/or a desired, an intensity of the emitted UVC radiation and the duration of exposure may be adjusted (set) to regulate a desired dosage of UVC delivered within the desired time window for sterilization of the display.

One or more UVC sensors may be positioned in the backlight unit 202 to detect UVC intensity during the operation of the LED engines 204 to generate the UVC. If the sensed intensity of the radiation is lower than a set intensity, it may be indicated that one or more LED engines may not be operating to provide the set intensity and the desired UVC dosage. In response to detection of a lower than set intensity of UVC, the intensity may be increased such that the desired dosage of UVC may still be delivered within the desired time window for sterilization of the display. The intensity of one or more operating (non-degraded) LED engines may be increased to compensate for the decreased dosage and to provide the desired dosage. A method for sanitizing the touchscreen is discussed in FIG. 14.

Figure 3:
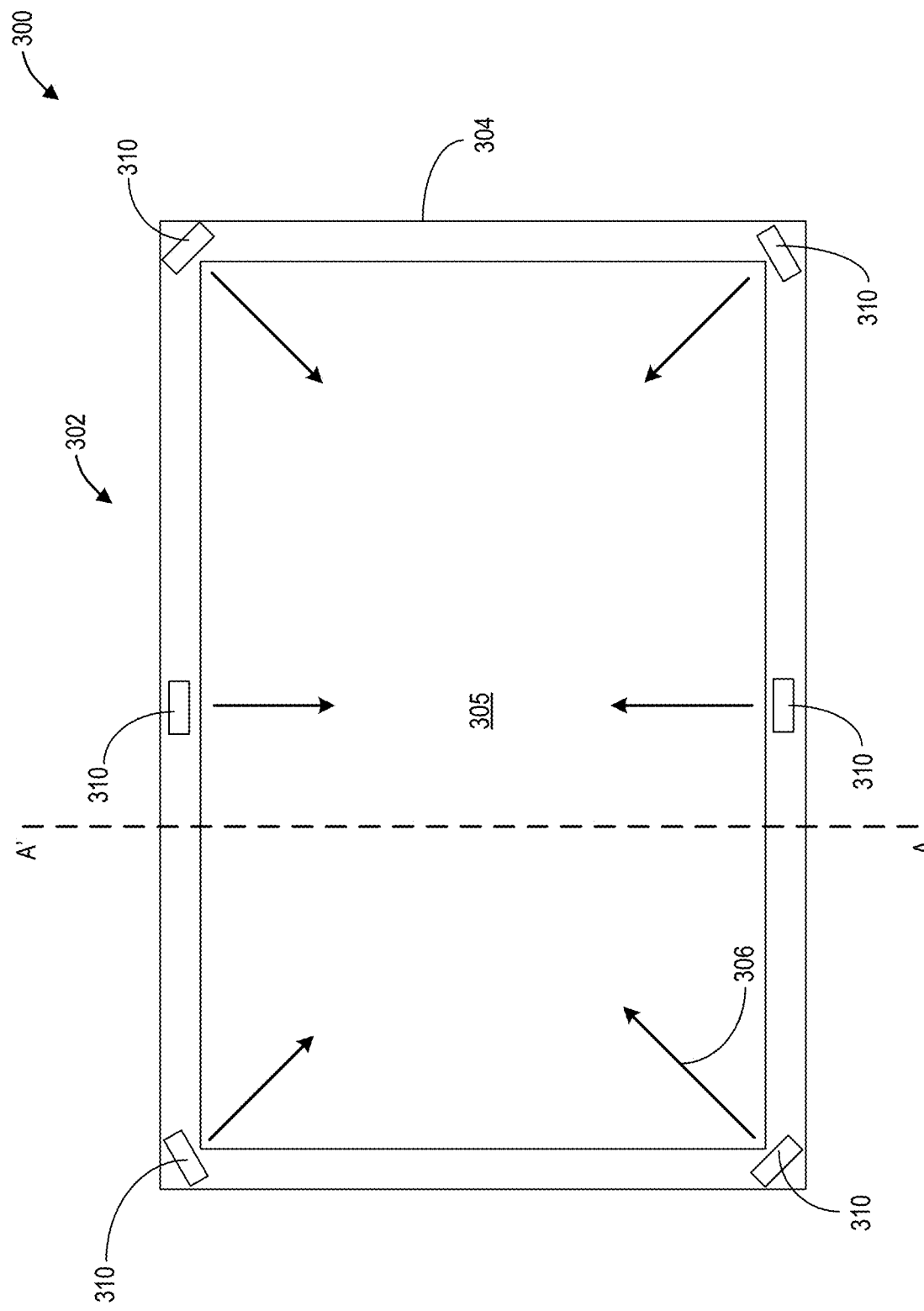
FIG. 3 shows a top view of a second embodiment of a self-sterilizing LCD display.

FIG. 3 shows a top view 300 of a second embodiment of a LCD assembly 302 including a self-sterilizing touchscreen 305. The LCD assembly 302 may be LCD assembly 103 of FIG. 1. In the second embodiment, the UVC emitting LED engines are integrated in a frame 304 around the perimeter of the touchscreen 305. The frame 304 may be an integral part of the LCD assembly 302 and may not be detached. The frame 304 may be coupled to the LCD assembly by solder joints and/or a combination of fasteners. The frame 304 may remain attached to the LCD assembly even when the touchscreen is not being sanitized by radiation of UVC by the LED engines. In one example, the LED engines may be integrated in a bezel of the touchscreen 305. As an example, the LED engines may be embedded in the bezel or frame of the touchscreen and may not be removed without disassembling the touchscreen including the bezel or frame.

The second embodiment of the LCD assembly 302 may include a structure similar to that of the first embodiment of the LCD assembly 201 as seen in FIG. 2. The touchscreen 305 in FIG. 2 may correspond to the touch panel 222 in FIG. 2. Each component of the first embodiment of the LCD assembly 201 may be included in the second embodiment of the LCD assembly 302 except the LED engines positioned within the backlight unit in first embodiment of the LCD assembly 201. In the second embodiment, the backlight unit may solely include visible light sources while the LEDs may be positioned along the perimeter of the touchscreen for generating UVC radiation (during sterilization of the touchscreen).

In one example, the LED engines 310 may be configured to radiate UVC light in the wavelength range of 200-222 nm through the surface of the touchscreen 305. In another example, an easily available and cost effective broadband LED light of wavelength 254 nm may be used in the backlight unit along with a layer of optical bandpass filter positioned along the frame 304 to selectively pass through UVC in the wavelength range 200-222 nm to the top layer of the display assembly. A first cross-section of the LCD assembly 201 including LEDs configured to radiate UVC light in the wavelength range of 200-222 nm taken along the dashed line A-A' is shown in FIG. 4A. A second cross-section of the LCD assembly 201 including LED engines configured to radiate UVC light in the wavelength range of 254 nm taken along the dashed line A-A' is shown in FIG. 4B.

In this example, six LED engines 310 are shown, however any number of LED engines may populate the periphery of the touchscreen 305. One or more LED engines may be parallel to the edge of the touchscreen 305 and one or more LED engines may be angularly placed along edges of the frame 304. The LED engines are configured in a way such that radiation from all the LED engines combined flood the entire surface of the touchscreen. At least one LED engine may illuminate each portion of the touchscreen 305.

Optical elements such as lenses may be positioned along the frame to reflect, focus, and/or disperse UVC radiation incident on the optical element towards the surface of the touchscreen 305. The inner surface of the wall of the frame 304 along the periphery of the frame 304 distal from the touchscreen 305 may be coated with a reflective material to reflect back all UVC radiation incident on it. By directly all of the UVC radiation to the surface of the touchscreen 305 and not allowing the radiation to be transmitted outside the display assembly 302, the entire dosage of UVC light may be used for sanitizing the touchscreen 305.

In one example, a cover or flap (not shown) may be used to cover the touchscreen 305 during generation of the UVC from the LEDs 310. By positioning the flap on the touchscreen 305, it may be indicated that a sanitizing routine is being carried out and the touchscreen 305 may not yet be sterilized and ready to be used by an operator.

A controller may be coupled to the display assembly 302 to operate the display assembly 302. The controller may be configured as a conventional microcomputer including a microprocessor unit, input/output ports, read-only memory, random access memory, keep alive memory, a controller area network (CAN) bus, etc. Power to operate the touchscreen and the LED engines may be provided through the controller.

FIG. 4A shows a first cross-sectional view 400 of the second embodiment of the self-sterilizing LCD display assembly 302 in FIG. 3 including LED engines 310 emitting light of a first wavelength. In LCD display assembly 302, the UVC emitting LED engines 310 are integrated in a frame 304 around the perimeter of the touchscreen 305. In this example, the LED engines 310 may be configured to radiate UVC light in the first wavelength range of 200-222 nm. UVC radiation in the wavelength range 200-222 nm may effectively sterilize the surface of the touchscreen 305 without being detrimental to human skin and eye sight. The frame 304 may be an integral part of the LCD assembly 302 and may not be detached. As an example, during assembly of the LCD assembly 203, the frame 304 may be coupled to the LCD assembly by solder joints and/or a combination of fasteners to form an integral part of the LCD assembly. The LCD assembly 302 may not be operated with the frame 304 being detached from the LCD assembly (such as during servicing or repair of the LCD assembly). The frame 304 may remain attached to the LCD assembly 302 even when the touchscreen is not being sanitized by radiation of UVC by the LED engines.

One or more optical directors 406 may be positioned along the frame 304 to direct UVC radiation 408 emitted from LED engines 310 onto the surface 416 (such as the surface that is touched by an operator) of the touchscreen 305. An optical director 406 may be angled relative to the horizontal interface of the touchscreen 305 and the frame 304. In this example, the optical director 406 makes an angle α with the horizontal interface of the touchscreen 305 and the frame 304, the angle α ranging from 10°-35°. The optical director 406 may be a single lens or a combination of optical elements configured to focus and/or diffract light radiation on it. The surface 416 of the touchscreen 305 may form the focal plane of the optical director 406 such that the UVC radiation 408 emitted from LED engines 310 may be focused by the optical director 406 onto the surface 416 of the touchscreen 305. Further surfaces of the frame that interface with air may be coated with a reflective material to reflect any UVC radiation incident on them and redirect the radiation to the touchscreen 305.

FIG. 4B shows a second cross-sectional view 450 of the second embodiment of the self-sterilizing LCD display assembly 302 in FIG. 3 including LED engines 410 emitting light of a second wavelength. In LCD display assembly 302, the UVC emitting LED engines 410 are integrated in a frame 304 around the perimeter of the touchscreen 305. In this example, the LED engines 410 may be configured to radiate UVC light in the second broadband wavelength of 254 nm. LED engines radiating 254 nm UVC radiation is commonly available and is cost effective. In order to maintain the wavelength of UVC radiation reaching the touchscreen 305 in the wavelength range 200-222 nm, an optical bandpass filter 470 may be positioned in face sharing contact with the frame 304 and adjacent to the touchscreen 305. All of the UVC radiation reaching the touchscreen 305 from the LED engine 410 may pass through the optical bandpass filter 470. The optical bandpass filter 470 is configured to only propagate UVC radiation in the wavelength range 200-222 nm while blocking all other wavelengths. As an example, the wavelength of radiation 458 incident on the optical bandpass filter 470 may be 254 nm while the wavelength of radiation incident on the touchscreen 305 may be in the wavelength range 200-222 nm. The change in wavelength of the UVC occurs while the radiation propagates through the optical bandpass filter 470. The frame 304 may be an integral part of the LCD assembly 302 and may not be detached.

FIG. 5A shows a first cross-sectional view 500 of a frame snapped on to a LCD display assembly 502 for sanitizing the LCD display assembly 502 including LED engines 504 emitting light of a first wavelength. In this example, the LED engines 504 are not integrated in a frame of the LCD display assembly 502, instead, the LED engines 504 may be integrated within a detachable frame 508.

The detachable frame 508 may be snapped onto the LCD display assembly 502 and may be removed when not in use. The same detachable frame 508 may be snapped onto multiple LCD devices. Upon attaching the detachable frame 508 to the LCD display assembly 502, the detachable frame 508 may line the perimeter of the touchscreen 505 of the LCD display assembly 502. The detachable frame 508 may be positioned along a bezel or an integrated frame of the LCD display assembly 502 when sterilization of a touchscreen 505 is desired. The LED engines 504 integrated in the detachable frame 508 may be powered via electricity from a cable that may be plugged in to an electric socket or other energy providing ports such as an USB port in the medical device including the LCD display assembly 502.

In this example, the LED engines 504 may be configured to radiate UVC light in the first wavelength range of 200-222 nm. UVC radiation in the wavelength range 200-222 nm may effectively sterilize the surface of the touchscreen 505 without being detrimental to human skin and eye sight. The LED engines 504 may be positioned parallel to an edge of the detachable frame 508 and not overlapping with the interface of the detachable frame 508 and the touchscreen 505. Upon activation of the LED engines, radiation 506 may wash over the touchscreen 505 and kill any microorganism contaminating the touchscreen 505.

FIG. 5B shows a second cross-sectional view 550 of a frame snapped on to a LCD display assembly 502 for sanitizing the LCD display assembly 502 including LED engines 554 emitting light of a second wavelength. In this example, the LED engines 554 are not integrated in a frame of the LCD display assembly 502, instead, the LED engines 554 may be integrated within a detachable frame 558.

The detachable frame 558 may be snapped onto the LCD display assembly 502 and may be removed when not in use. Upon attaching the detachable frame 558 to the LCD display assembly 502, the detachable frame 558 may line the perimeter of the touchscreen 505 of the LCD display assembly 502. The detachable frame 558 may be positioned along a bezel or an integrated frame of the LCD display assembly 502 when sterilization of a touchscreen 505 is desired. The LED engines 554 integrated in the detachable frame 558 may be powered via electricity from a cable that may be plugged in to an electric socket or other energy providing ports such as an USB port in the medical device including the LCD display assembly 502.

The LED engines 554 may be positioned parallel to an edge of the detachable frame 508 and not overlapping with the interface of the detachable frame 508 and the touchscreen 505. In this example, the LED engines 554 may be configured to radiate UVC light in the second broadband wavelength of 254 nm. LED engines radiating 254 nm UVC radiation is commonly available and is cost effective. In order to maintain the wavelength of UVC radiation reaching the touchscreen 505 in the wavelength range 200-222 nm, an optical bandpass filter 562 may be positioned along edge of the frame 558 in face sharing contact with the LED engines 554 and adjacent to the touchscreen 305. The LED engine 554 may be embedded within the frame 558 while the optical bandpass filter 562 may be external to the frame 558.

All of the UVC radiation reaching the touchscreen 505 from the LED engine 554 may pass through the optical bandpass filter 562. The optical bandpass filter 562 is configured to only propagate UVC radiation in the wavelength range 200-222 nm while blocking all other wavelengths. As an example, the wavelength of radiation emitted from the LED engine 554 may be 254 nm while the wavelength of radiation incident on the touchscreen 505 may be in the wavelength range 200-222 nm. The change in wavelength of the UVC occurs while the radiation propagates through the optical bandpass filter 562.

FIG. 6 shows a first example 600 of a cooling system 601 for a LED engine 604 used for self-sterilizing a LCD display. LED engine 604 may be LED engine 310, 410, 504, or 554 in FIGS. 4A, 4B, 5A, and 5B respectively. In this example, the cooling system may be a liquid, coolant based cooling system used to cool one or more LED engines. In this example, a single LED engine 604 is shown, however in alternate examples multiple LED engines may be cooled in series or in parallel arrangement.

LED engines are solid state devices that directly convert electricity to light. A LED engine 604 may include a solid LED chip 614 mounted on a substrate 638, the chip 614 being the active component that produces the light. The substrate may be made of a ceramic material. Similar to a diode, the chip 614 includes an anode and a cathode and is activated by a forward voltage. The voltage generates a current and a conversion from electricity to light is made at a p-n junction. A wavelength of light generated may be based on the applied voltage. In this example, a UVC light is generated by the LED engine 604. As examples, the UVC light may be in the range of 200-222 nm or 254 nm.

The substrate 638 and the LED chip 614 may be mounted on a heat slug 639 to facilitate thermal dissipation. The heat slug may be made of a thermally conductive material such as copper. A pair of LED leads 616 or bonding wires may be positioned on each side of the LED chip 614. A hemispherical lens 612 enclosing the LED chip 614 may be positioned over the substrate 638. The lens 612 may focus and/or diffract the light emitted by the LED chip 614. The interspace between the lens 612 and the chip 614 may be filled with silicone to protect the chip 614 and LED leads 616. A sealant or thermal potting compound 624 may be used to seal and isolate the LED engine 604 from the atmosphere. The sealant or thermal potting compound 624 may be positioned on each side of the LED leads 616 enclosing the LED leads 616. As electricity is converted to light, a part of the electrical energy may be dissipated as heat. Overheating of the LED engine 604 may cause degradation of the components. A cooling system may be associated with the LED engine 604 to dissipate the heat generated. The sealant or thermal potting compound 624 may also facilitate in heat dissipation from the LED engine 604.

The LED engine 604 may be directly coupled to a liquid based cooling system 601. The cooling system 601 may be integrated into the frame (such as frame 304 in FIG. 3) or backing of a LCD display assembly (such as LCD display assembly 302 in FIG. 3), a touchscreen of the LCD assembly sterilized using UVC radiation from the LED engine 604.

The cooling system 601 may include a heat exchanger 606 through which a liquid coolant may be circulated. Coolant flowing through the heat exchanger 606 may absorb heat dissipated from the LED engine 604 and then flow to a radiator 608 via a first coolant line 641. Since the coolant absorbs heat at the heat exchanger 606, the coolant entering the radiator 608 is at a higher temperature. The radiator 608 may include a fan 609 that circulate cooling air through the radiator 608. Heat from the coolant is dissipated at the radiator 608 and the temperature of the coolant reduces. The cooled coolant is routed back to the heat exchanger 606 via a second coolant line 640. A pump 642 may be housed in the second coolant line 640 to facilitate flow of coolant from the radiator 608 to the heat exchanger 606.

The heat exchanger 606 may include a hollow central region 646 enclosed within a housing 634 including copper channels. The hollow central region 646 may optionally include a heat dissipating sintered wick 636 positioned directly below the LED engine 604. The top surface of the sintered wick 636 may be coupled to the heat slug 639 of the LED engine 604 via a solder joint 622. Cold coolant may enter the central region 646 via the second coolant line 640 and after flowing through the sintered wick 636, the heated coolant may exit the heat exchanger via the first coolant line 641. The surface of the heat exchanger (upper surface) proximal to the LED engine 604 may include a layer 630 of copper cladding. The disjointed layer 630 of copper cladding may extend on each side of the sintered wick 636. The layer 630 may be coupled to the LED leads 616 on each side of the LED engine 604 via solder joints 622. A layer 632 of dielectric material may be sandwiched within the layer 630 of copper cladding to allow thermal dissipation without being electrically conductive. Heat from the LED engine 604 components such as the chip 614 and the LED leads 616 may be conducted to the coolant flowing through the heat exchanger 606 via one or more of the heat slug 639, the sintered wick 636, and the layer 630 of copper cladding wherein the heat may be dissipated to the flowing coolant. In this way, heat generated at the LED engine 694 may be effectively removed and possibility of overheating of the engine may be reduced.

FIG. 7 shows a cross-section of a first example 700 of a heat pipe arrangement for cooling a LED engine 604 used for self-sterilizing a LCD display. LED engine 604 may be LED engine 310, 410, 504, or 554 in FIGS. 4A, 4B, 5A, and 5B. In this example, a single LED engine 604 is shown, however in examples multiple LED engines may be cooled in series or in parallel arrangement via the heat pipe 710. Identical components of the LED engine 604 previously described in FIG. 6 are not reintroduced in FIG. 7.

The heat pipe 710 may include a hollow, cylindrical core 712 with a layer of sintered wick 714 lining an inner wall of the heat pipe 710. Heatsink fins 720 may enclose the heat pipe 710 at a first end of the heat pipe 710. The heatsink fins 720 may be coupled to the heat pipe 710 via a solder joint 704 including a thermal interface material. The heatsink fins 720 may dissipate heat to a radiator 716 including a fan.

The heat slug 639 and/or a portion of the substrate 638 of the LED engine 604 may be coupled to an outer wall of the heat pipe 710 at a location upstream of the heatsink fins 720 via a shoulder joint 704, a layer of copper cladding 706, and a layer of a dielectric material 708. The layer of dielectric material 708 may be in contact with the heat pipe 710. In this example, the LED engine 604 is indirectly mated with the heat pipe due to the presence of intermediate layers such as the layer of copper cladding 706 and the layer of a dielectric material 708. Heat from the LED engine 604 may be dissipated to a working fluid flowing through the core 712 of the heat pipe 710 via the layer of copper cladding 706 and the layer of a dielectric material 708. As the heat is absorbed by the working fluid (in liquid form), the liquid vaporizes and the vapor flows towards the region of the heat pipe 710 concentric with the heatsink fins 720, as shown by the solid arrows. The heat pipe 710 may be tilted downwards to facilitate the flow of the fluid vapors from the region of the heat pipe 710 in contact with the LED engine 604 to the region of the heat pipe 710 concentric with the heatsink fins 720.

Heat from the vapor may be dissipated at the heatsink fins 720 while heat from the heatsink fins may be dissipated to the associated radiator 716. As the heat is dissipated from the vapor, the working fluid may condense from vapor state to liquid state. The working fluid in the liquid state may return to the region of the heat pipe 710 in contact with the LED engine 604 via the sintered wick 714 lining by capillary effect, as shown by the dashed lines. The cycle of heat absorption, vaporization of working fluid, and condensation of working fluid may be continued to remove heat generated at the LED engine 604.

FIG. 8 shows a cross-section of a second example 800 of a heat pipe arrangement for cooling a LED engine 604 used for self-sterilizing a LCD display. LED engine 604 may be LED engine 310, 410, 504, or 554 in FIGS. 4A, 4B, 5A, and 5B. In this example, a single LED engine 604 is shown, however in examples multiple LED engines may be cooled in series or in parallel arrangement via the heat pipe 710. Identical components of the LED engine 604 previously described in FIG. 6 are not reintroduced in FIG. 7. Identical components of the heat pipe 710 previously described in FIG. 8 are not reintroduced in FIG. 8.

The heat slug 639 and/or a portion of the substrate 638 of the LED engine 604 may be directly coupled to an outer wall of the heat pipe 710 at a location upstream of the heatsink fins 720 via a shoulder joint 704 (without any intermediate layers). A first layer of dielectric material 804 may be positioned between a first LED lead 616 of the LED engine 604 on one side and the outer wall of the heat pipe 710 and a second layer of dielectric material 806 may be positioned between a second LED lead 617 of the LED engine 604 on another side and the outer wall of the heat pipe 710. Each of the first layer of dielectric material 804 and the second layer of dielectric material 806 may be coupled to the respective LED leads via solder joints 704.

In this example, the LED engine 604 is directly mated with the heat pipe without the presence of intermediate layers. Heat from the chip of the LED engine 604 may be directly dissipated from the LED engine 604 to a working fluid flowing through the core 712 of the heat pipe 710. Heat from the leads 616, 617 of the LED engine 604 may be dissipated from the LED engine 604 to a working fluid flowing through the core 712 of the heat pipe 710 via the layers of dielectric material 804, 806. As the heat is absorbed by the working fluid (in liquid form), the liquid vaporizes and the vapor flows towards the region of the heat pipe 710 concentric with the heatsink fins 720, as shown by the solid arrows.

Heat from the vapor may be dissipated at the heatsink fins 720 while heat from the heatsink fins may be dissipated to the associated radiator 716. As the heat is dissipated from the vapor, the working fluid may condense from vapor state to liquid state. The working fluid in the liquid state may return to the region of the heat pipe 710 in contact with the LED engine 604 via the sintered wick 714 lining by capillary effect, as shown by the dashed arrows. The cycle of heat absorption, vaporization of working fluid and condensation of working fluid may be continued to remove heat generated at the LED engine 604.

FIG. 9 shows a top down view 900 of a LCD display assembly 902 including a heat pipe 710 for cooling one or more LED engines 604. The LCD assembly 902 may include a self-sterilizing touchscreen 905. In one example, the LCD assembly 902 is the LCD assembly 302 in FIG. 3. One or more the UVC emitting LED engines 604 may be integrated in a frame 904 around the perimeter of the touchscreen 905. In one example, the frame 904 may be an integral part of the LCD assembly 902 and may not be detached. In another example, the frame 904 may be a separate (detachable) unit that may be snapped on and removed from the perimeter of the LCD assembly 902. In one example, the LED engines may be integrated in a bezel of the touchscreen 905.

One or more optical elements such as lens 908 may be coupled to the frame 904 adjacent to the LED engine 604 to focus and/or diffract the UVC radiation emitting from the LED engine. The UVC radiation 910 may be focused onto a surface 916 of the touchscreen 905 to disinfect the surface 916 touchscreen 905 that is touched by an operator. The surface 916 of the touchscreen 905 may form the focal plane of the optical elements 908 such that the UVC radiation 910 emitted from LED engine 604 may be focused by the optical elements 908 onto the surface 916 of the touchscreen 905.

In this example, a single LED engine 604 is shown, however in other example multiple LED engines are lined along the frame 904. Identical components of the LED engine 604 previously described in FIG. 6 are not reintroduced in FIG. 9. A heat pipe 710 may be included within the frame 904 with an outer surface of the heat pipe in direct or indirect thermal contact with the LED engine 604. Example of heat pipes with direct and indirect thermal mating are shown in FIGS. 7 and 8 respectively. A first region 912 of the heat pipe 710 may be in contact with the LED engine 604 while a second region 914 of the heat pipe 710 may be in contact with heatsink fins 718. As heat is generated at the LED engine 604, the heat is dissipated to a working fluid in the heat pipe 710 at the first region 912 and the heat from the working fluid may be dissipated via the heatsink fins 718 at the second region 914 of the heat pipe 710.

FIG. 10A shows a first example 1000 of a heat sink 1002 for cooling a LED engine 604 used for self-sterilizing a LCD display. LED engine 604 may be LED engine 310, 410, 504, or 554 in FIGS. 4A, 4B, 5A, and 5B. In this example, a single LED engine 604 is shown, however in examples multiple LED engines may be coupled to the same heat sink 1002. Identical components of the LED engine 604 previously described in FIG. 6 are not reintroduced in FIG. 7. The LED engine 604 and the associated heat sink 1002 may be integrated in a frame around the LCD display.

The heat sink 1002 may include a printed circuit board (PCD) made of a composite material substrate 1012 such as a FR-4 substrate. The composite material substrate 1012 may be sandwiched between an upper layer 1006 of copper cladding and a lower layer 1008 of copper cladding. An array of thermal vias 1010 may be drilled through the composite material substrate 1012 connecting the upper layer 1006 of copper cladding and a lower layer 1008 of copper cladding. The lower layer 1008 of copper cladding may be coupled to heatsink fins 1014 positioned directly below the array of thermal vias 1010 via solder joint 1004.

The heat slug 639 and/or a portion of the substrate 638 of the LED engine 604 may be coupled to the upper layer 1006 of copper cladding via a layer of solder joint 1004. The LED engine 604 may be positioned directly above the thermal vias 1010 in the composite material substrate 1012. Heat generated at the LED engine 604 may be dissipated to the heatsink fins 1014 via the upper layer 1006 of copper cladding, the array of thermal vias 1010, and the lower layer 1008 of copper cladding. In this way, heat from the LED engine 604 may be effectively dissipated and possibility of overheating of LED engine components may be reduced.

FIG. 10B shows a second example 1050 of a heat sink 1052 for cooling a LED engine 604 used for self-sterilizing a LCD display. LED engine 604 may be LED engine 310, 410, 504, or 554 in FIGS. 4A, 4B, 5A, and 5B. In this example, a single LED engine 604 is shown, however in examples multiple LED engines may be coupled to the same heat sink 1052. Identical components of the LED engine 604 previously described in FIG. 6 are not reintroduced in FIG. 7. The LED engine 604 and the associated heat sink 1052 may be integrated in a frame around the LCD display.

The heat sink 1002 may include a first layer of copper cladding 1006 positioned above a second layer of a dielectric material 1052. The dielectric material may be in face sharing contact with a metal plate 1054. The thickness of the metal plate 1054 may be higher than that of the first layer of copper cladding 1006 and the second layer of a dielectric material 1052. The metal plate 1054 may be coupled to heatsink fins 1014.

The heat slug 639 and/or a portion of the substrate 638 of the LED engine 604 may be coupled to the metal plate 1054. The LED engine 604 may be positioned directly above heatsink fins 1014. Heat generated at the LED engine 604 may be dissipated to the heatsink fins 1014 via the first layer of copper cladding 1006, the second layer of a dielectric material 1052, and the metal plate 1054. In this way, heat from the LED engine 604 may be effectively dissipated and possibility of overheating of LED engine components may be reduced.

FIG. 11 shows a cross-sectional view 1100 of a LCD assembly 1116 including a heat sink 1002 for cooling an LED engine 604. The LCD assembly 1116 may include a self-sterilizing touchscreen 1005. In one example, the LCD assembly 1116 is the LCD assembly 302 in FIG. 3. One or more the UVC emitting LED engines 604 may be integrated in a frame 1102 around the perimeter of the touchscreen 1005. In one example, the frame 1102 may be an integral part of the LCD assembly 1116 and may not be detached. In another example, the frame 1102 may be a separate (detachable) unit that may be snapped on and removed from the perimeter of the LCD assembly 1116. In one example, the LED engines may be integrated in a bezel of the touchscreen 1105.

Identical components of the LED engine 604 previously described in FIG. 6 are not reintroduced in FIG. 11. UVC radiation 1114 may be emitted from the LED engine 604 and directed to a surface 1124 (surface 1124 may be contaminated from touch) of the touchscreen 1105 via focusing and/or diffracting lens 1106 enclosing the LED engine 604. The surface 1124 of the touchscreen 1105 may form the focal plane of the lens 1106 such that the UVC radiation 1114 emitted from LED engine 604 may be focused by the lens 1106 onto the surface 1124 of the touchscreen 1105.

A first inverted L-shaped reflective surface 1110 may partially enclose the lens 1106 to reflect any of the UVC radiations incident on it. Further a layer of opaque material 1108 may be coated on the reflective surface 1110 to avert any of the UVC radiations from escaping the assembly without being directed to the touchscreen 1105. By ensuring that the entire dosage of UVC radiation emitted from the LED engine 604 reaches the touchscreen 1005, sterilization of the touchscreen may be facilitated.

In this example, a single LED engine 604 is shown, however in other example multiple LED engines may be lined along the frame 904. A heat sink 1002 for cooling an LED engine 604 may be included within the frame 1104. The components of the heat sink 1002 are described previously in FIG. 10A. In another example, the heat sink 1052 of FIG. 10B may also be used in place of heat sink 1002 for cooling the LED engine 604.

FIG. 12 shows a first example schematic of a layout 1200 of passageways (channels) for fluidic cooling of one or more LED engines. In one example, the passageways may be machined or molded into a rear housing of a LCD display assembly. In another example, the passageways may be machined or molded into a frame including the one or more LED engines that may be snapped onto the LCD display assembly. In this example, four LED engines (first LED engine 1204, second LED engine 1206, third LED engine 1208, and fourth LED engine 1210) are shown connected to the passageways for dissipating heat generated at the respective LED engines during operation. Each of the first LED engine 1204, second LED engine 1206, third LED engine 1208, and fourth LED engine 1210 may be LED engine 604 in FIG. 6. UVC radiation from one or more of the first LED engine 1204, second LED engine 1206, third LED engine 1208, and fourth LED engine 1210 may be used to sterilize a touchscreen of the LCD display assembly.

Cooled fluid (coolant) may exit a radiator 1225 via a first passage 1224 and enter a pump 1225. The cooled fluid may exit the pump 1225 via a second passage 1232, the second passage diverting into a third passage 1240 supplying cooled fluid to the first LED engine 1204 and a fourth passage 1238 supplying cooled fluid to the second LED engine 1206. Cooled fluid may also exit the pump 1225 via a fifth passage 1234 to be supplied to the third LED engine 1208. Cooled fluid may further exit the pump 1225 via a sixth passage 1236 to be supplied to the fourth LED engine 1210.

After flowing through and collecting heat from the first LED engine 1204, heated fluid may return to the radiator 1221 via a seventh passage 1220 and an eighth passage 1218. After flowing through and collecting heat from the second LED engine 1206, heated fluid may return to the radiator 1221 via a ninth passage 1222 and the eighth passage 1218. After flowing through and collecting heat from the third LED engine 1208, heated fluid may return to the radiator 1221 via a tenth passage 1212 and the eighth passage 1218. After flowing through and collecting heat from the fourth LED engine 1210, heated fluid may return to the radiator 1221 via an eleventh passage 1214 and the eighth passage 1218. Heat from the heated fluid may be dissipated at the radiator 1221. In one example, the radiator may include a fan to circulate ambient air through the radiator 1221. The cooled fluid may then be circulated back to the LED engines via the pump 1225.

FIG. 13 shows a second example layout 1300 of passageways for fluidic cooling of one or more LED engines. In one example, the passageways may be machined or molded into a rear housing of a LCD display assembly. In another example, the passageways may be machined or molded into a frame including the one or more LED engines that may be snapped onto the LCD display assembly. In this example, four LED engines (first LED engine 1306, second LED engine 1308, third LED engine 1310, and fourth LED engine 1312) are shown connected to the passageways in series for dissipating heat generated at the respective LED engines during operation. Each of the first LED engine 1306, the second LED engine 1308, the third LED engine 1310, and the fourth LED engine 1312 may be LED engine 604 in FIG. 6. UVC radiation from one or more of the first LED engine 1306, the second LED engine 1308, the third LED engine 1310, and the fourth LED engine 1312 may be used to sterilize a touchscreen of the LCD display assembly. In other examples, fewer or more LED engines may be positioned within along the cooling passageway.

A single cooling passage 1320 may flow a cooling fluid through each of the first LED engine 1306, the second LED engine 1308, the third LED engine 1310, and the fourth LED engine 1312 in series. Heat from each of the LED engines may be dissipated to the cooling fluid flowing through the LED engines via the passage 1320. After flowing through the fourth LED engine 1312, the heated fluid may be pumped through a radiator 1304 wherein the heat from the fluid may be dissipated. The radiator may include a fan to circulate ambient air through the radiator 1304. After being cooled at the radiator 1304, the cooled fluid may then be circulated back to the series of LED engines.

Arrays of extruded heatsink fins may be thermally connected to the cooling passage 1320 to dissipate heat from the cooling fluid flowing through the cooling passage 1320. A first array of heatsink fins 1336 may overlap with the first LED engine 1306, a second array of heatsink fins 1332 may overlap with the second LED engine 1308, a third array of heatsink fins 1336 may overlap with the third LED engine 1310 to dissipate heat from the respective LED engines. One or more LED engines such as the fourth LED engine 1312 may not directly dissipate heat to an array of heatsink fins but may dissipate their entire heat to the cooling fluid flowing through them. Arrays of heatsink fins 1334 may overlap with the cooling passage 1320 to remove heat from the cooling liquid. Further an array of heatsink fins 1338 may overlap with the radiator 1304 to facilitate in disperse thermal energy from the radiator 1304 thereby cooling the cooling fluid flowing through the radiator 1304.

FIG. 14 shows an example method 1400 for sanitizing a touchscreen of a LCD display assembly using UVC radiation generated form one or more LED engines. The touchscreen of the LCD display assembly may be configured (as a user interface) to present visual information such as in the form of text and graphics to an operator (also referred herein as user) of a medical device. The medical device may be the ventilator system in FIG. 1. The touchscreen display may be used by multiple operators to enter commands during operation of the medical device. In one example, the LCD display assembly may be the LCD assembly 201 in FIG. 2 wherein the UVC emitting LEDs are integrated in the LCD assembly. In another example, the LCD display assembly may be the LCD display 302 in FIGS. 4A, 4B wherein the UVC emitting LED engines are integrated in a frame around the perimeter of the touchscreen. In yet another example, the LCD display assembly may be the LCD display 502 in FIGS. 5A, 5B wherein the UVC emitting LED engines are integrated in a detachable frame snapped on around the perimeter of the touchscreen. Each of the LED engines may be configured as a LED 604 in FIG. 6.

At 1402, the routine includes determining if sanitizing of the touchscreen is desired. In one example, sterilization of the touchscreen may be desired upon selection of a sterilization cycle by a user via inputs to the touchscreen or via inputs to a remote device (such as smart phone or tablet) wirelessly connected to the medical device. In another example, sterilization cycles may be pre-scheduled such as at regular intervals of time (such as every six or twelve hours) or during certain medical procedures. Sterilization may be carried out while operating the medical device during certain medical procedures. In yet another example, sterilization of the touchscreen may be desired upon completion of use of the medical device by an operator before another operator resumes use of the medical device. In a further example, sterilization of the touchscreen may be desired upon completion of use of the medical device for a patient before the device is used for another patient. As an example, upon completion of a workflow and use of the medical device by a user, the user may be prompted to request sanitization of the touchscreen such as via inputs to the touchscreen or via inputs to the remote device. The prompt may be in the form of a pop up message on the LCD display of the device.

If it is determined that sterilization of the touchscreen is not desired, at 1404, the LED engines are maintained inactive and UVC is not generated. If it is determined that sterilization of the touchscreen is desired, at 1406, the user may be prompted to select a duration or mode of sterilization. As an example, options for sterilization may include two or more modes of sterilization cycles with each mode corresponding to a dosage of UVC delivered. In one example, a first mode may correspond to a higher UVC dosage while a second mode may correspond to a lower UVC dosage. The first mode may be selected if a higher level of contamination is present or if a longer duration of time is available before next use of the device. The second mode may be selected if a lower level of contamination is present or if a shorter duration of time is available before next use of the device. The degree of sterilization (destruction of microorganisms by UVC) is directly proportional to the dosage of the UVC. If the sterilization is pre-scheduled, the prompt for selecting a mode or duration of sterilization may not be provided. The mode or duration of sterilization may be predetermined during the scheduling.

At 1408, intensity of UVC generated by the LEDs and a duration of generation of the UVC during the sterilization cycle may be selected based on the selected mode or duration of sterilization. The dosage of UVC generated is directly proportional to the intensity of the radiation and the duration of the radiation. The relationship between a dosage of UVC and an intensity of UVC is given by equation 1.

$$D=I*t \quad (1)$$

where D is the dosage of UV radiation, I is the intensity of UVC radiation, and t is the exposure time. In one example, if a mode with a higher dosage is selected and/or a shorter time is available for the sterilization cycle, a higher intensity of UVC may be selected. In another example, if a mode with a lower dosage is selected and/or a longer time is available for the sterilization cycle, a higher intensity of UVC may be selected. In yet another example, if a shorter duration of the sterilization cycle is selected, the UVC intensity may be selected based on a lowest possible UVC dosage desired for destruction of microorganisms. In a further example, if the sterilization cycle is to be carried out during use of the device, a lower intensity of the UVC over a longer duration may be selected for effective sterilization. The selected intensity may not be constant throughout the duration of the sterilization cycle but may be modulated over the duration such as by providing increased intensity at the onset of the cycle and then reducing the intensity over time. As an example, a look-up table may be used to estimate the intensity of the UVC radiation with dosage and duration as inputs and intensity as output. Further, the UV intensity and duration of exposure can also be defined/programmed remotely such as by a medical professional. Example sterilization cycles may run for a duration between 5-20 mins.

At 1410, the user may be optionally prompted to position a shield or a cover over the touchscreen during the sterilization cycle. The shield (such as a flap) may ensure UVC radiations not being propagated beyond the device. However, since the UVC radiations in the range of 200 nm-220 nm used for sterilization may not be detrimental to human skin or eyes, sterilization of the touchscreen may be carried out without covering the touchscreen. Also, for pre-scheduled and timed sterilization cycles, a user may not be available to position the shield over the touchscreen.

At 1412, UVC radiation at the selected intensity may be initiated by activating the one or more LED engines supplying UVC radiation to the touchscreen. The UVC radiation may substantially (such as more 90%) cover the entire surface area of the touchscreen in contact with a user during operation such that the entire touchscreen may be disinfected. UVC of wavelength in the range of 200 nm-220 nm may be used during the sterilization cycle. At 1414, upon completion of the duration of the sterilization cycle, emission of UVC radiation may be terminated by disabling the LED engines. Upon completion of the sterilization cycle, microorganisms previously contaminating the touchscreen may be destructed and the medical device may be ready to be used by another operator and/or for a different patient.

In this way, a method for a touchscreen of a liquid crystal display in a ventilator system, comprises: selecting a mode or duration of sanitizing of the touchscreen, and covering substantially an entire surface area of the touchscreen with an ultra violet radiation in a wavelength range of 200 nm-222 nm generated via a series of light emitting diode (LED) engines positioned along a perimeter of the touchscreen, an intensity of the UV radiation adjusted based on the selected mode or duration of the sterilization of the touchscreen.

In one example, a method, comprising: a request for sanitization of a touchscreen included in a liquid crystal display (LCD) assembly of a medical device, generating ultraviolet light of a first wavelength from one or more light emitting diode (LED) engines positioned along a perimeter of the touchscreen or integrated in the LCD assembly, the ultraviolet (UV) light flooding the touchscreen to sanitize the touchscreen. In the preceding example, additionally or optionally, the first wavelength of ultraviolet light is in a range from 200 nm to 222 nm. In any or all of the preceding examples, additionally or optionally, generating ultraviolet light of the first wavelength includes emitting a broadband UV light of 254 nm wavelength from the one or more LED engines and then passing the broadband UV light through one or more bandpass filters to generate UV light of the first wavelength, one of the one or more bandpass filters positioned adjacent to one of the one or more LED engines. In any or all of the preceding examples, additionally or optionally, the one or more LED engines are integrated along a frame or bezel of the touchscreen, the frame or bezel being an integral part of the LCD assembly. In any or all of the preceding examples, additionally or optionally, the one or more LED engines are integrated along a detachable frame of the touchscreen, the detachable frame snapped on to the LCD assembly during the sanitization of the touchscreen. In any or all of the preceding examples, additionally or optionally, the UV light generated from the one or more LED engines positioned along the perimeter of the LCD assembly is focused onto the touchscreen via one or more optical directors. In any or all of the preceding examples, additionally or optionally, the one or more LED engines are integrated in a backlight unit of the LCD assembly, the UV light travelling through an array of liquid crystals, polarizers, and quartz substrates to reach a touchscreen panel of the LCD assembly. In any or all of the preceding examples, additionally or optionally, the request for sanitization is in response to a sanitization cycle being selected by an operator via an input to the touchscreen or via an input to a device wirelessly connected to the LCD assembly. In any or all of the preceding examples, additionally or optionally, a user is prompted for the request for sanitization, the prompting in response to an end of a workflow and completion of use of the medical device by an operator or a patient. In any or all of the preceding examples, the method further comprising, additionally or optionally, adjusting an intensity of the UV light based on a duration of sanitization of the touchscreen and a desired dosage of the UV light, the intensity of the UV light increasing with an increase in the desired dosage and a decrease in the duration of sanitization. In any or all of the preceding examples, additionally or optionally, the medical device is one of a ventilator system and an anesthesia machine.

In another example, a system for a LCD assembly of a medical device, comprises: a touchscreen panel including a frame lining a perimeter of the touchscreen panel, the touchscreen panel used by an operator during operation of the medical device, a series of LED engines integrated in the frame of the touchscreen panel generating ultra violet radiation of a first wavelength, and a series of optical lenses corresponding to the series of the LED engines focusing the UV radiation onto the touchscreen panel, the focused UV radiation washing over substantially an entire surface area of the touchscreen panel facing the operator. In the preceding example, additionally or optionally, the generating of the UV radiation is in response to one of the operator initiating a sanitizing cycle of the touchscreen panel and an onset of a pre-scheduled sanitization cycle. In any or all of the preceding examples, additionally or optionally, the frame of the touchscreen panel is detachable from the LCD assembly, the frame usable with a plurality of separate touchscreen panels. In any or all of the preceding examples, additionally or optionally, each LED engine of the series of LED engines dissipate heat to a cooling liquid flowing through a heat exchanger integrated into the frame of the touchscreen panel. In any or all of the preceding examples, additionally or optionally, each LED engine of the series of LED engines dissipate heat to a heat pipe integrated into the frame of the touchscreen panel, each LED engine directly or indirectly thermally mating with the heat pipe. In any or all of the preceding examples, additionally or optionally, each LED engine of the series of LED engines dissipate heat via a heat sink including one or more of thermal vias, a metal plate, and heatsink fins. In any or all of the preceding examples, additionally or optionally, the first wavelength of generated UV radiation is in a range of 200-222 nm.

In yet another example, a method for a touchscreen of a liquid crystal display in a ventilator system, comprises: selecting a mode or duration of sanitizing of the touchscreen, and covering substantially an entire surface area of the touchscreen with an ultra violet radiation in a wavelength range of 200 nm-222 nm generated via a series of light emitting diode (LED) engines positioned along a perimeter of the touchscreen, an intensity of the UV radiation adjusted based on the selected mode or duration of the sanitization of the touchscreen. In the preceding example, additionally or optionally, the mode and duration of sanitizing of the touchscreen is selected based on a desired dosage of UV radiation, the dosage of UV radiation being directly proportional to each of the intensity of the UV radiation and the duration of sanitization.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

I claim:

1. A method, comprising:
   in response to a request for sanitization of a touchscreen included in a liquid crystal display (LCD) assembly of a medical device, generating ultraviolet light of a first wavelength from one or more light emitting diode (LED) engines positioned along a perimeter of the touchscreen or integrated in the LCD assembly, the ultraviolet (UV) light flooding the touchscreen to sanitize the touchscreen,
   wherein the one or more LED engines are integrated in a backlight unit of the LCD assembly, the UV light travelling through an array of liquid crystals, polarizers, and quartz substrates to reach a touchscreen panel of the LCD assembly.

2. The method of claim 1, wherein the first wavelength of ultraviolet light is in a range from 200 nm to 222 nm.

3. The method of claim 1, wherein generating ultraviolet light of the first wavelength includes emitting a broadband UV light of 254 nm wavelength from the one or more LED engines and then passing the broadband UV light through one or more bandpass filters to generate UV light of the first wavelength, one of the one or more bandpass filters positioned adjacent to one of the one or more LED engines.

4. The method of claim 1, wherein the one or more LED engines are integrated along a frame or bezel of the touchscreen, the frame or bezel being an integral part of the LCD assembly.

5. A method, comprising:
   in response to a request for sanitization of a touchscreen included in a liquid crystal display (LCD) assembly of a medical device, generating ultraviolet light of a first wavelength from one or more light emitting diode (LED) engines positioned along a perimeter of the touchscreen or integrated in the LCD assembly, the ultraviolet (UV) light flooding the touchscreen to sanitize the touchscreen,
   wherein the one or more LED engines are integrated along a detachable frame of the touchscreen, the detachable frame snapped on to the LCD assembly during the sanitization of the touchscreen.

6. The method of claim 1, wherein the UV light generated from the one or more LED engines positioned along the perimeter of the LCD assembly is focused onto the touchscreen via one or more optical directors.

7. The method of claim 1, wherein the request for sanitization is in response to a sanitization cycle being selected by an operator via an input to the touchscreen or via an input to a device wirelessly connected to the LCD assembly.

8. The method of claim 1, wherein a user is prompted for the request for sanitization, the prompting in response to an end of a workflow and completion of use of the medical device by an operator or a patient.

9. The method of claim 1, further comprising, adjusting an intensity of the UV light based on a duration of sanitization of the touchscreen and a desired dosage of the UV light, the intensity of the UV light increasing with an increase in the desired dosage and a decrease in the duration of sanitization.

10. The method of claim 1, wherein the medical device is one of a ventilator system and an anesthesia machine.

11. A method for a touchscreen of a liquid crystal display in a ventilator system, comprising:

selecting a mode or duration of sanitizing of the touchscreen, and covering substantially an entire surface area of the touchscreen with an ultra violet radiation in a wavelength range of 200 nm-222 nm generated via a series of light emitting diode (LED) engines positioned along a perimeter of the touchscreen, an intensity of the UV radiation adjusted based on the selected mode or duration of the sanitization of the touchscreen, wherein the series of LED engines are integrated in a backlight unit of the LCD assembly, the UV radiation travelling through an array of liquid crystals, polarizers, and quartz substrates to reach a touchscreen panel of the LCD assembly.

12. The method of claim 11, wherein the mode and duration of sanitizing of the touchscreen is selected based on a desired dosage of UV radiation, the dosage of UV radiation being directly proportional to each of the intensity of the UV radiation and the duration of sanitization.

* * * * *